(12) United States Patent
Hsia

(10) Patent No.: US 12,029,765 B2
(45) Date of Patent: *Jul. 9, 2024

(54) COMPOSITIONS AND METHODS FOR TREATING CANCER

(71) Applicant: Houn Simon Hsia, Tustin, CA (US)

(72) Inventor: Houn Simon Hsia, Tustin, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/986,496

(22) Filed: Nov. 14, 2022

(65) Prior Publication Data

US 2023/0124019 A1 Apr. 20, 2023

Related U.S. Application Data

(63) Continuation of application No. 17/161,447, filed on Jan. 28, 2021, now Pat. No. 11,541,079, which is a continuation of application No. 16/007,509, filed on Jun. 13, 2018, now Pat. No. 10,905,723, which is a continuation of application No. 16/007,539, filed on Jun. 13, 2018, now Pat. No. 10,905,725.

(60) Provisional application No. 62/670,275, filed on May 11, 2018, provisional application No. 62/595,002, filed on Dec. 5, 2017, provisional application No. 62/519,087, filed on Jun. 13, 2017, provisional application No. 62/519,096, filed on Jun. 13, 2017, provisional application No. 62/519,093, filed on Jun. 13, 2017.

(51) Int. Cl.
| | | |
|---|---|---|
| *A61K 35/60* | (2006.01) | |
| *A23L 33/115* | (2016.01) | |
| *A23L 33/16* | (2016.01) | |
| *A61K 33/04* | (2006.01) | |
| *A61P 35/04* | (2006.01) | |
| *A61N 5/10* | (2006.01) | |

(52) U.S. Cl.
CPC ............ *A61K 35/60* (2013.01); *A23L 33/115* (2016.08); *A23L 33/16* (2016.08); *A61K 33/04* (2013.01); *A61P 35/04* (2018.01); *A23V 2002/00* (2013.01); *A61N 5/10* (2013.01)

(58) Field of Classification Search
CPC ..... A61N 5/10; A23V 2002/00; A23L 33/115; A23L 33/16; A61P 35/04; A61K 33/04; A61K 35/60
See application file for complete search history.

(56) References Cited

U.S. PATENT DOCUMENTS

| | | | |
|---|---|---|---|
| 6,077,828 A | 6/2000 | Abbruzzese | |
| 6,197,295 B1 | 3/2001 | Hsia | |
| 6,576,233 B2 | 6/2003 | Hsia | |
| 8,257,694 B2 | 9/2012 | Daikeler | |
| 9,072,768 B2 | 7/2015 | Ranganathan | |
| 10,206,861 B2 * | 2/2019 | Seiberg | A61K 8/347 |
| 10,905,723 B2 * | 2/2021 | Hsia | A61K 35/60 |
| 10,905,725 B2 | 2/2021 | Hsia | |
| 2005/0013875 A1 | 1/2005 | Kobayashi | |
| 2006/0034944 A1 | 2/2006 | Ruslow | |
| 2007/0116802 A1 | 5/2007 | Germano | |
| 2011/0189220 A1 | 8/2011 | Yang | |
| 2011/0195093 A1 | 8/2011 | Gunn | |
| 2011/0229447 A1 | 9/2011 | Schiffrin | |
| 2014/0294795 A1 | 10/2014 | Hsia | |

FOREIGN PATENT DOCUMENTS

| | | | |
|---|---|---|---|
| CN | 101569410 | 11/2009 | |
| CN | 101687017 | 3/2010 | |
| CN | 102164595 | 8/2011 | |
| CN | 105617358 | 6/2016 | |
| CN | 105768108 A | 7/2016 | |
| CN | 106822560 * | 6/2017 | ......... A61K 36/8966 |
| DE | 2020013002760 U1 | 7/2014 | |
| JP | 6340544 | 6/1996 | |
| JP | 20121479 | 1/2012 | |
| JP | 2019529578 | 10/2019 | |
| KR | 20040073559 | 8/2004 | |
| TW | 201141501 | 12/2011 | |
| WO | 2011115062 A1 | 9/2011 | |
| WO | 2012018597 | 2/2012 | |
| WO | 2012122295 | 9/2012 | |
| WO | 2018231937 | 12/2018 | |
| WO | 2018231943 | 12/2018 | |

OTHER PUBLICATIONS

CN106822560 Machine Translation (Year: 2017).*
Farukh Durrani, et al, Synergistic Effect of Selenium Compounds with Radiation Therapy in Human A549 Lung Xenografts, 67 Cancer Res. Issue 9 Supp. (Year: 2007).*
Hang Wang, et al, Reduction of Splenic Immunosuppressive Cells and Enhancement of Anti-Tumor Immunity by Synergy of Fish Oil and Selenium Yeast, 8 PLOS ONE 1 (Year: 2013).*
Charles Simone, et al, Antioxidants and Other Nutrients Do Not Interfere with Chemotherapy or Radiation Therapy and Can Increase Kill and Increase Survival, Part 2, 13 Alt. Therapies Health Med. 40 (Year: 2007).*
Calviello, G, et al. "Antineoplastic effects of N-3 polyunsaturated fatty acids in combination with drugs and radiotherapy: preventive abd therapeutic strategies," Nutrition and Cancer61:3, 287-301. 16 pages.
Fernandes, et al. "Selenium coumpounds as therapeutic agents in cancer," Biochimica et Biophysica Acta. 19 pages.
Tran, et al. "Immune targeting of fibroblast activation protein triggers recognition of multipotent bone marrow stromal cells and cachexia," The Journal of Experimental Medicine. 11 pages.
Nair, et al., "Methylseleninic Acid Sensitizes Ovarian Cancer Cells to T-Cell Mediated Killing by Decreasing PDL1 and VEGF Levels," Frontiers in Oncology. 12 pages.

(Continued)

*Primary Examiner* — Sean M Basquill
(74) *Attorney, Agent, or Firm* — Fish IP Law, LLP

(57) ABSTRACT

A nutritional supplement containing fish oil and selenium has been identified that reduces angiogenesis and/or stem cell content of tumors. A formulation for such a supplement that is both well tolerated and palatable is also provided.

4 Claims, 40 Drawing Sheets

(56) References Cited

OTHER PUBLICATIONS

Extended European Search Report dated May 28, 2021, from related application 18817547.5. 17 pages.
Wang, Hang, et al. "Reduction of splenic immunosuppressive cells and enhancement of anti-tumor immunity by synergy of fish oil and selenium yeast," PLoS ONE 8(1):e52912. 10 pages.
Hwang, Jin-Taek, et al. Selenium Regulates Cyclooxygenase-2 and Extracellular Signal-Regulated Kinase Signaling Pathways by Activating AMPActivated Protein Kinase in Colon Cancer Cells. www.aacrjournals.org. Cancer Res 2006; 66: (20).Oct. 15, 2006. 7 pages.
Douwes, Friedrich. "Integrative Cancer Therapy Concept at St. George Hospital Germany," Klinik St. Georg. 6 pages.
Fahmy, et al. "Protective Effects of ro-3 fatty acids and/ or Nano-selenium on Cisplatin and Ionizing radiation induced liver toxicity in rats," Indian Journal or Pharmaceutical Education and Research. vol. 50, Issue 4, Oct.-Dec. 2016.
Tallarida, Ronald J. "Drug Synergism and Dose-Effect Data Analysis." 29 pages.
Aristi, et al. "Selenium Compounds as therapeutic agents in cancer." 19 pages.
"Nutritional assessment and nutritional support for patients with malignant tumor." 8 pages.
"Research progress on nutritional risk and nutritional therapy in patients with gastric cancer." 6 pages.
Extended European Search Report dated Feb. 1, 2021, from related application 18817307.4. 6 pages.
Fakih, et al. "Selenium Protects Against Toxicity Induced by Anticancer Drugs and Augments Antitumor Activity: A Highly Selective, New, and Novel Approach for the Treatment of Solid Tumors," Clinical Colorectal Cancer, vol. 5, No. 2, 132-135. 2005. 4 pages.
Norman, et al. "The Role of Dietary Supplements during Cancer Therapy," International Research and Conference on Food, Nutrition, and Cancer. American Society for Nutritional Sciences, 2003. 6 pages.
Fernandes, et al. "Selenium compunds as therapeutic agents in cancer," Biochimica et Biophysica Acta. 2014. 19 pages.
Pardini, Ronals S. Nutiritional intervention with omega-3 fatty acids enhances tumor response to anti-neoplastic agents. ScienceDirect, Chemico-Biological Interactions, 162, 2006, 89-105. 17 pages.

* cited by examiner

| | | | Scarify (14th day) | Scarify (24th day) |
|---|---|---|---|---|
| 1 | C | control | N=6 | N=6 |
| 2 | T | Tumor | N=6 | N=6 |
| 3 | TN | Tumor + Nutrawell | N=6 | N=6 |
| 4 | T3R | Tumor + Radiotherapy x3 | N=6 | N=6 |
| 5 | T3RN | Tumor + Radiotherapy x3 + Nutrawell | N=6 | N=6 |

|     | Bax | Bcl-2 | Bax/Bcl-2 | Caspase 3 |
| --- | --- | --- | --- | --- |
| T   | 0.31±0.00 | 1.41±0.67 | 0.22±0.12 | 1.03±0.88 |
| TN  | 5199.29±2321.78 | 241.89±7.44 | 21.49±10.19 | 47708.35±7808.87 |
| TR  | 1.09±1.39 | 0.99±0.16 | 1.10±0.03 | 0.71±0.06 |
| TRN | 7858.24±1593.75 | 213.40±8.45 | 36.82±9.56 | 46977.1±5263.41 |

FIG. 14

| | | | Sacrifice (21st day) |
|---|---|---|---|
| 1 | C | Control | N=6 |
| 2 | T | Tumor | N=6 |
| 3 | PTN | Tumor + Nutrawell (-7 day start) | N=6 |
| 4 | TN | Tumor + Nutrawell (0 day start) | N=6 |
| 5 | TR | Tumor + Radiotherapy (3 Gy x 3) | N=6 |
| 6 | PTRN | Tumor + Radiotherapy (3 Gy x 3) + Nutrawell (-7 day start) | N=6 |
| 7 | TRN | Tumor + Radiotherapy (3 Gy x 3) + Nutrawell (8 day start) | N=6 |

| | | | Scarify (24th day) |
|---|---|---|---|
| 1 | C | Control | N=6 |
| 2 | T | Tumor | N=6 |
| 3 | TN | Tumor + Nutrawell | N=6 |
| 4 | TR | Tumor + Radiotherapy x3 | N=6 |
| 5 | TRN | Tumor + Radiotherapy x3 + Nutrawell | N=6 |

| | | | Sacrifice (21st day) |
|---|---|---|---|
| 1 | C | Control | N=6 |
| 2 | T | Tumor | N=6 |
| 3 | PTN | Tumor + Nutrawell (-7 day start) | N=6 |
| 4 | TN | Tumor + Nutrawell (0 day start) | N=6 |
| 5 | TR | Tumor + Radiotherapy (3 Gy x 3) | N=6 |
| 6 | PTRN | Tumor + Radiotherapy (3 Gy x 3) + Nutrawell (-7 day start) | N=6 |
| 7 | TRN | Tumor + Radiotherapy (3 Gy x 3) + Nutrawell (8 day start) | N=6 |

COMPOSITIONS AND METHODS FOR TREATING CANCER

This application is a continuation of U.S. patent application Ser. No. 17/161,447, file Jan. 28, 2021, which is a continuation of U.S. Pat. No. 10,905,723, filed Jun. 13, 2018, which claims the benefit of U.S. Provisional Application No. 62/519,087 filed on Jun. 13, 2017, and of U.S. patent application Ser. No. 16/007,539, filed Jun. 13, 2018, which claims the benefit of U.S. Provisional Application No. 62/519,093, filed on Jun. 13, 2017, U.S. Provisional Application No. 62/519,096, filed on Jun. 13, 2017, U.S. Provisional Application No. 62/595,002 filed on Dec. 5, 2017, and U.S. Provisional Application No. 62/670,275 filed on May 11, 2018. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is cancer therapy.

BACKGROUND

The background description includes information that may be useful in understanding the present invention. It is not an admission that any of the information provided herein is prior art or relevant to the presently claimed invention, or that any publication specifically or implicitly referenced is prior art.

Radiotherapy and chemotherapy protocols utilized in the treatment of cancer can clearly benefit patients, but can be ineffective or less effective with some cancers. In addition both radiotherapy and chemotherapy are associated with significant side effects, including nausea, weight loss, hair loss, damage to the gastrointestinal tract, and skin irritation.

Attempts have been made to enhance the effectiveness of radiotherapy. For example, gold nanoparticles that have been modified to target tumor cells have been used to enhance radiotherapy (Yang et al, ACS Nano, 2014, 8(9): 8992-9002). All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply. Similarly, COX-2 inhibitors have been used to selectively sensitize tumor cells to the effects of radiation (Choy and Milas, J. Natl Cancer Inst (2003) 95(19):1140-1452). Such approaches, however, can have issues with selectivity and may not be effective against all tumor types. To date attempts to reduce the side effects of radiotherapy are primarily directed to partitioning the total radiation dose into a number of smaller radiation doses (leaving time in between to allow for recovery), targeting of tumor using shielding, and identification of the boundaries of the tumor and localization of radiotherapy to that site. Unfortunately, such approaches can fail to adequately treat all of the tumor cells.

Attempts have also been made to enhance the effects of chemotherapy. Some studies have suggested that consumption of fish oil can improve results from chemotherapy, however other research has suggested that fish oil can interfere (Daenen et al, JAMA Oncol (2015) 1(3):350-358). Formulation of chemotherapeutic agents as nanoparticles has also been attempted (Xu et al, Coll. Surf. B: Biointerfaces (2006) 48(1):50-57). It is unclear, however, if all chemotherapeutic drugs are suitable for such reformulation. Codelivery of chemotherapeutic drugs with siRNA designed to interfere with multi-drug resistance has also been explored. Such siRNAs, however, are sequence specific and may not be suitable for some tumors.

Mitigation of the side effects of chemotherapy are generally directed at providing symptomatic relief. For example, antiemetics can be used to reduce nausea, along with diet modification and eating small, frequent meals that avoid certain foods. Unfortunately such approaches are not always effective. In some instances chemotherapeutic agents are selected to have reduced toxicity in order to reduce side effects, however such agents may also have reduced effectiveness against tumor cells.

Thus, there is still a need for safe and effective compositions and methods to enhance the effectiveness and/or reduce the side effects of cancer radiotherapy and/or chemotherapy.

SUMMARY OF THE INVENTION

The inventive subject matter provides compositions and methods treating cancer through the use of a nutritional supplement containing fish oil and selenium, in some embodiments in combination with radiotherapy.

Embodiments of the inventive concept can include methods of reducing angiogenesis a tumor by applying a radiotherapy protocol to a patient in need of treatment while providing the patient with a nutritional supplement containing fish oil and selenium (for example, as shown in Table 1). In some embodiments the nutritional supplement is provided to the patient prior to the initiation of radiotherapy. Such a nutritional supplement can be formulated such that two or more, or all of the components of the supplement are provided in amounts as described in Table 1.

Another embodiment of the inventive concept is a method of reducing metastasis from a tumor, by providing the patient having a metastatic tumor with a nutritional supplement that includes fish oil and selenium (such as in Table 1) where the nutritional supplement is provided in an amount to reduce metastatic activity of the tumor. In some embodiments such a nutritional supplement is provided either prior to or at the initiation of radiotherapy, and can be provided through the course of radiotherapy. In a preferred embodiment the nutritional supplement is formulated such that two or more of the supplement's components are provided in amounts as described in Table 1.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 1 depicts a treatment protocol in which nutritional supplementation is provided starting either 7 days prior to implementation of radiotherapy or simultaneously with tumor cell implantation. Mice were sacrificed 21 days after tumor cell implantation.

FIG. 2A depicts changes in body weight over time for various treatment groups. FIG. 2B depicts change in body weight in various treatment groups over the course of the study. Note that body weight is reported following removal of the primary tumor mass.

FIGS. 3A to 3D show typical synergistic effects on tumor volume and weight of co-treatment with radiotherapy and the supplement containing fish oil and selenium. FIG. 3A shows changes in tumor volume over time for various treatment groups. FIG. 3B provides a detailed view of the first 11 days of treatment as shown in FIG. 3A. FIG. 3C provides a histogram of tumor weight for various treatment groups. FIG. 3D provides photographs of exemplary tumors from various treatment groups.

FIG. 4A: Effect of treatment using radiotherapy, a supplement containing fish oil and selenium, and combined treatment on gastrocnemius muscle mass 21 days after tumor cell injection. FIG. 4B: Effect of treatment using radiotherapy, a supplement containing fish oil and selenium, and combined treatment on soleus muscle mass 21 days after tumor cell injection. FIG. 4C: Effect of treatment using radiotherapy, NutraWell supplement, and combined treatment on lung (inclusive of metastatic tumor) weight 21 days after tumor cell injection. FIG. 4D: Effect of treatment using radiotherapy, NutraWell supplement, and combined treatment on liver (inclusive of metastatic tumor) weight 21 days after tumor cell injection. FIG. 4E: Effect of treatment using radiotherapy, NutraWell supplement, and combined treatment on spleen (inclusive of metastatic tumor) weight 21 days after tumor cell injection. FIG. 4F provides quantitative results of studies of lung metastasis in animal subjects treated with a supplement containing fish oil and selenium and/or radiotherapy. FIG. 4G shows the results of studies of Ki-67 expression in primary tumor sites and metastatic sites in animal subjects treated with a supplement containing fish oil and selenium and/or radiotherapy.

FIG. 5A: Effect of treatment using radiotherapy, NutraWell supplement, and combined treatment on platelet count 21 days after tumor cell injection. FIG. 5B: Effect of treatment using radiotherapy, NutraWell supplement, and combined treatment on white blood cell count 21 days after tumor cell injection. FIG. 5C: Effect of treatment using radiotherapy, NutraWell supplement, and combined treatment on lymphocyte count 21 days after tumor cell injection. FIG. 5D: Effect of treatment using radiotherapy, NutraWell supplement, and combined treatment on granulocyte count 21 days after tumor cell injection. FIG. 5E: Effect of treatment using radiotherapy, NutraWell supplement, and combined treatment on neutrophil/lymphocyte percentage ratio 21 days after tumor cell injection.

FIG. 6A: Effect of treatment using radiotherapy, NutraWell supplement, and combined treatment on serum albumin 21 days after tumor cell injection. FIG. 6B: Effect of treatment using radiotherapy, NutraWell supplement, and combined treatment on serum creatinine 21 days after tumor cell injection.

FIG. 7A: Effect of treatment using radiotherapy, NutraWell supplement, and combined treatment on serum IL-6 21 days after tumor cell injection. FIG. 7B: Effect of treatment using radiotherapy, NutraWell supplement, and combined treatment on serum IL-1β 21 days after tumor cell injection.

FIG. 8A: Effect of treatment using radiotherapy, NutraWell supplement, and combined treatment on expression of the VEGF gene in an implanted tumor 21 days after tumor cell injection. FIG. 8B: Effect of treatment using radiotherapy, NutraWell supplement, and combined treatment on expression of the BAX gene in an implanted tumor 21 days after tumor cell injection. FIG. 8C: Effect of treatment using radiotherapy, NutraWell supplement, and combined treatment on expression of the Bcl-2 gene in an implanted tumor 21 days after tumor cell injection. FIG. 8D: Effect of treatment using radiotherapy, NutraWell supplement, and combined treatment on expression of the caspase 3 gene in an implanted tumor 21 days after tumor cell injection. FIG. 8E: Effect of treatment using radiotherapy, NutraWell supplement, and combined treatment on expression of the BAX gene in lung 21 days after tumor cell injection. FIG. 8F: Effect of treatment using radiotherapy, NutraWell supplement, and combined treatment on expression of the Bcl-2 gene in lung 21 days after tumor cell injection.

FIG. 8G: Effect of treatment using radiotherapy, NutraWell supplement, and combined treatment on expression of the caspase 3 gene in lung 21 days after tumor cell injection.

FIG. 9A depicts a testing protocol in which mice receive radiotherapy on days 8, 10, and 12, with nutritional supplementation beginning with the initiation of radiotherapy. Mice are sacrificed at day 14 or at day 24 following implantation of tumor cells. FIG. 9B: Treatment groups derived from the protocol shown in FIG. 9A.

FIG. 10A: Serum albumin concentration at 14 days and 24 days following tumor cell implantation in mice treated as shown in FIG. 9A. FIG. 10B: Lymphocyte counts at 14 days and 24 days following tumor cell implantation in mice treated as shown in FIG. 9A. FIG. 10C: N/L Ratio at 14 days and 24 days following tumor cell implantation in mice treated as shown in FIG. 9A.

FIG. 11A: VEGF expression within the tumor mass 24 days following tumor cell implantation in mice treated as shown in FIG. 9A. FITC represents VEGF-specific staining. FIG. 11B: VEGF expression within the lung (metastasis) 24 days following tumor cell implantation in mice treated as shown in FIG. 9A. FITC represents VEGF-specific staining. FIG. 11C: EGFR expression within the lung (metastasis) 24 days following tumor cell implantation in mice treated as shown in FIG. 9A. FITC represents EGFR-specific staining. FIG. 11D: EGFR expression within the tumor mass 24 days following tumor cell implantation in mice treated as shown in FIG. 9A. FITC represents EGFR-specific staining.

FIG. 13AA shows the presence of H1F1-α (hypoxia marker) protein within the tumor mass and in lung tissue (metastasis) 24 days following tumor cell implantation in mice treated as shown in FIG. 9A. FITC represents H1F1-α-specific staining.

FIG. 13B shows results of gene expression studies of tumor samples from subjects treated with a nutritional supplement containing fish oil and selenium and/or radiotherapy.

FIG. 14: Expression of apoptosis markers 24 days following tumor cell implantation in mice treated as shown in FIG. 9A.

FIG. 15A shows the results of studies characterizing PDL-1 gene expression in primary and metastatic tumor sites in animal models of human disease treated with a supplement containing fish oil and selenium and/or radiotherapy. FIG. 15B shows the results of studies characterizing PD-1 gene expression in primary and metastatic tumor sites in animal models of human disease treated with a supplement containing fish oil and selenium and/or radiotherapy.

FIG. 16A depicts a testing protocol in which mice receive radiotherapy on days 8, 10, and 12, with nutritional supplementation provided prior to tumor cell implantation, at the time of tumor cell implantation, or at the initiation of radiotherapy. Mice are sacrificed at day 21 following implantation of tumor cells. FIG. 16B: Treatment groups derived from the protocol shown in FIG. 16A.

FIG. 18A: Effect of treatment using radiotherapy, NutraWell supplement, and combined treatment on expression of the VEGF gene 21 days after tumor cell injection. FIG. 18B: Effect of treatment using radiotherapy, NutraWell supplement, and combined treatment on expression of the BAX gene 21 days after tumor cell injection. FIG. 18C: Effect of treatment using radiotherapy, NutraWell supplement, and combined treatment on expression of the Bcl-2 gene 21 days after tumor cell injection. FIG. 18D: Effect of treatment using radiotherapy, NutraWell supplement, and combined treatment on expression of the Caspase 3 gene 21 days after tumor cell injection. FIG. 18E: Effect of treatment using radiotherapy, NutraWell supplement, and combined treatment on expression of the Bcl-2 gene 21 days in lung (i.e. metastasis) after tumor cell injection. FIG. 18F: Effect of treatment using radiotherapy, NutraWell supplement, and combined treatment on expression of the Caspase 3 gene 21 days in lung (i.e. metastasis) after tumor cell injection.

FIG. 19A depicts a testing protocol in which mice receive radiotherapy on days 8, 10, and 12, with nutritional supplementation provided for 7 days prior to tumor cell implantation. Mice are sacrificed at day 24 following implantation of tumor cells. FIG. 19B: Treatment groups derived from the protocol shown in FIG. 19A.

FIG. 20A: Effect of a nutritional supplement containing fish oil and selenium on body mass in mice receiving repeated radiotherapy following tumor cell implantation using the protocol shown in FIG. 19A. FIG. 20B: Effect of treatment using radiotherapy, a nutritional supplement containing fish oil and selenium, and combined treatment on gastrocnemius muscle mass 21 days after tumor cell injection using the protocol shown in FIG. 19A.

FIG. 21A depicts a testing protocol mice in which mice receive radiotherapy on days 8, 10, and 12, with nutritional supplementation provided for 7 days prior to, the day of, or 8 days after tumor cell implantation. Mice are sacrificed at day 21 following implantation of tumor cells. FIG. 21B: Treatment groups derived from the protocol shown in FIG. 21A.

FIG. 24A: Effect of treatment using repeated radiotherapy in combination with NutraWell supplement, and combined treatment on serum TNF-α 21 days after tumor cell injection in mice treated using the protocol shown in FIG. 21A. FIG. 24B: Effect of treatment using repeated radiotherapy in combination with NutraWell supplement, and combined treatment on serum IL-6 21 days after tumor cell injection in mice treated using the protocol shown in FIG. 21A.

DETAILED DESCRIPTION

Figure 1:
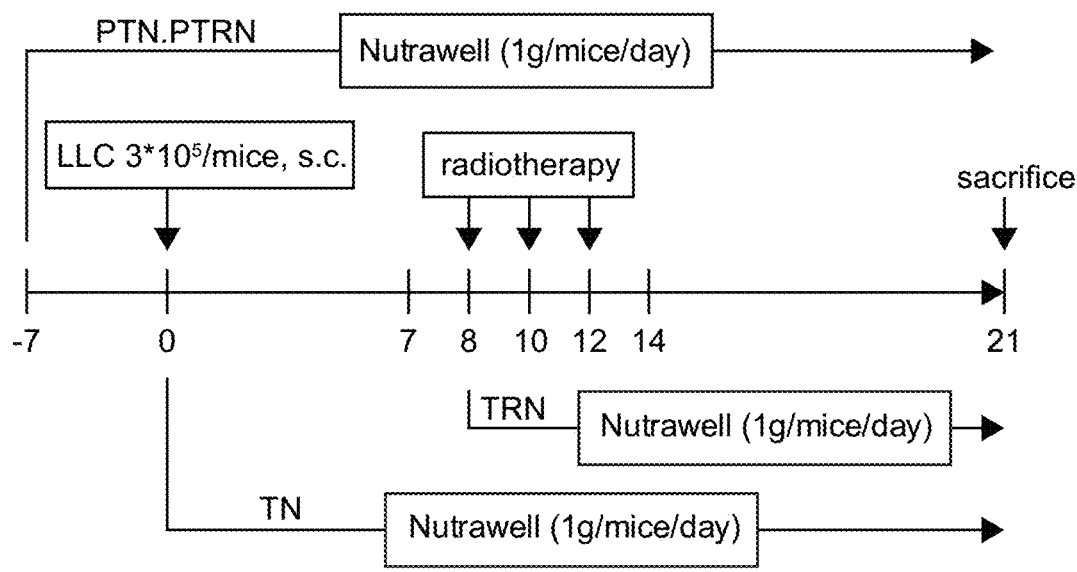
FIG. 1.

The following description includes information that may be useful in understanding the present invention. It is not an admission that any of the information provided herein is prior art or relevant to the presently claimed invention, or that any publication specifically or implicitly referenced is prior art.

The inventive subject matter provides compositions and methods in which a nutritional supplement that includes fish oil and selenium (for example, a supplement containing fish oil, selenium derived from selenium yeast, and certain vitamins, minerals, amino acids, and saccharides, e.g. "NutraWell") is used in combination with radiotherapy. Combination therapy with radiation and such a supplement surprisingly provides a significant synergistic effect in reduction of tumor size. In addition, side effects of radiotherapy (e.g. neutropenia, loss of body mass, loss of muscle mass, damage to acyl cells of the gastrointestinal tract, etc.) are reduced and/or mitigated relative to application of radiotherapy without use of such a supplement. Surprisingly, expression of genes related to angiogenesis and apoptosis were also found to be modulated in tumor cells on use of a supplement containing fish oil and selenium, both with and without the application of radiotherapy. In addition, metastasis is prevented and the growth and spread of cancer stem cells was found to be reduced.

One should appreciate that the disclosed techniques provide many advantageous technical effects including enhancing the effectiveness of current radiotherapeutic protocols used in the treatment of cancer while reducing the side effects associated with these approaches.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In one embodiment of the inventive concept, a nutritional supplement composition as shown in Table 1 ("Nutrawell") is provided to improve the results of radiotherapy.

TABLE 1

| Component | Minimum | Maximum | Unit |
|---|---|---|---|
| Maltodextrin | 10000 | 50000 | mg |
| Whey Protein Isolate | 5000 | 60000 | mg |
| Whey Protein Concentrate | 1000 | 50000 | mg |
| Fructooligosaccharides/Inulin | 40 | 15000 | mg |
| Granulated Honey | 1000 | 9000 | mg |
| Oat Fiber | 500 | 15000 | mg |
| Natural French Vanilla Flavor | 500 | 20000 | mg |
| Soy Protein | 500 | 50000 | mg |
| Brownulated Powdered Brown Sugar | 500 | 10000 | mg |
| Natural Vanilla Masking Flavor | 500 | 5000 | mg |
| Lecithin | 200 | 10000 | mg |
| Milk, Non-fat | 50 | 5000 | mg |
| Rice Protein Powder | 50 | 5000 | mg |
| Calcium Caseinate | 50 | 2000 | mg |
| Oils | | | |
| Flax Seed Oil | 100 | 7000 | mg |
| Canola Oil | 100 | 7000 | mg |
| Borage Oil | 100 | 7000 | mg |
| Olive Oil | 100 | 7000 | mg |
| Fish Oil | 150 | 10,000 | mg |
| Pure Lemon Oil | 100 | 1000 | mg |
| Pure Orange Oil | 50 | 1000 | mg |
| Mixed Tocopherols | 0.5 | 200 | mg |
| Vitamins/Minerals | | | |
| Potassium Phosphate | 200 | 1500 | mg |
| Calcium Carbonate | 100 | 5000 | mg |
| Choline Bitartrate | 150 | 2500 | mg |
| Sodium Chloride | 100 | 2000 | mg |
| Calcium Phosphate Tribasic | 100 | 2000 | mg |
| Ascorbic Acid | 50 | 3000 | mg |
| Potassium Chloride | 50 | 2000 | mg |
| Magnesium Oxide | 50 | 500 | mg |
| Selenium Yeast | 30 | 4000 | mcg |
| Chromium Yeast | 30 | 3000 | mcg |
| Molybdenum Yeast | 30 | 2000 | mcg |
| Inositol | 10 | 5000 | mg |
| Zinc Sulfate Monohydrate | 5 | 200 | mg |
| Dry Vitamin E Acetate | 5 | 2000 | IU |
| Niacinamide | 5 | 500 | mg |
| Ferric Orthophosphate | 3 | 100 | mg |
| Calcium Pantothenate | 3 | 200 | mg |
| Manganese Sulfate Monohydrate | 3 | 100 | mg |
| Beta Carotene | 1 | 100 | mg |
| Copper Gluconate | 1 | 15 | mg |
| Vitamin D3 | 25 | 5000 | IU |
| Vitamin K2 | 2 | 1000 | mcg |
| Pyridoxine HCl | 0.5 | 200 | mg |
| Potassium Iodide | 0.5 | 1500 | mg |
| Riboflavin | 0.5 | 1000 | mg |
| Thiamine Hydrochloride | 0.5 | 2500 | mg |
| Dry Vitamin K1 | 1 | 500 | mcg |
| Vitamin A Acetate | 500 | 100000 | IU |
| Folic Acid | 100 | 10000 | mcg |
| d-Biotin | 10 | 10000 | mcg |
| Vitamin B12 | 1 | 3000 | mcg |
| Amino Acids | | | |
| L-Carnitine | 300 | 30000 | mg |
| L-Glutamine | 500 | 60000 | mg |
| L-Arginine Base | 500 | 30000 | mg |
| Taurine | 50 | 2000 | mg |
| L-Lysine | 50 | 2000 | mg |
| Alpha Lipoic Acid | 10 | 1000 | mg |
| Resveratrol | 15 | 1500 | mg |
| Co-Enzyme Q10 | 10 | 5000 | mg |
| Glycine | 5 | 1000 | mg |
| Proline | 5 | 1000 | mg |
| Bacterial Cultures | | | |
| Lact. Acidophilus (app. 10 billion total) | 2 | 500 | mg |
| Bifido Bifidium (app. 10 billion total) | 2 | 500 | mg |

TABLE 1-continued

| Component | Minimum | Maximum | Unit |
|---|---|---|---|
| Lac. Bulgaricus (app. 10 billion total) | 2 | 500 | mg |
| Bifido Longum (app. 10 billion total) | 2 | 500 | mg |
| Strep. Thermophilus (app. 10 billion total) | 2 | 500 | mg |
| Enzymes | | | |
| Papain | 5 | 100 | mg |
| Pepsin | 5 | 100 | mg |
| Lipase | 5 | 100 | mg |
| Bromelain | 5 | 100 | mg |
| Pancreatin 4X | 0.5 | 100 | mg |
| Lactase | 1 | 100 | mg |
| Betaine HCl | 3 | 100 | mg |
| Plant Products | | | |
| Pineapple Juice Powder | 2 | 500 | mg |
| Papaya Fruit Powder | 2 | 500 | mg |
| Quercetin | 30 | 3000 | mg |
| EGCG | 25 | 600 | mg |
| OPC | 15 | 500 | mg |
| Anthocyanins | 15 | 5000 | mg |
| Ellagic Acid | 10 | 300 | mg |
| Astaxanthin | 2 | 90 | mg |
| Fucoidan | 20 | 1500 | mg |
| Mushroom Preparation | | | |
| Cordyceps | 5 | 6000 | mg |
| Ganoderma Lucidum | 15 | 10000 | mg |
| Shiitake | 40 | 15000 | mg |
| Maitake | 30 | 15000 | mg |
| Turkey Tail | 30 | 15000 | mg |

The composition shown in Table 1 includes components that have various physiological and biochemical effects, including anti-inflammatory activity, lowering of blood glucose levels, lowering of cholesterol, and anti-tumor activity. Other components provide supplementation of necessary vitamins, minerals, and amino acids at elevated levels. Other components (e.g. enzymes, lecithin) serve to aid in digestion and absorption of components of the composition when consumed. The combination of these complementary activities provides a synergistic effect that exceeds the simple additive effect of individual components. It should be appreciated that the composition shown in Table 1 also includes certain flavorants (e.g. brown sugar, honey, vanilla flavor and masking agent) that serve to improve palatability and acceptance. Certain components (e.g. honey, brown sugar, milk, rice protein, casein) can provide both flavor and caloric energy. The Inventor has found that the combination of flavorants described above is effective in providing compliance with consumption of the nutritional supplement in effective amounts. In some embodiments, such flavorants can be excluded without negatively impacting the effectiveness of the nutritional supplement.

Components shown in Table 1 can be provided as a single formulation (for example, as a pill, tablet, capsule, powder, liquid, suspension, etc.) or can be segregated into different formulations (for example, as pills, tablets, capsules, powders, liquids, suspensions, or combinations thereof). The amounts shown in Table 1 are exemplary, and represent typical daily dosages provided to an adult of normal stature and otherwise normal health. These amounts can be adjusted to account for differences in body mass, gender, medical condition, etc. For example, a relatively small patient weighing 40 kilos or less may receive benefit from dosages provided at or below the low end of the ranges provided, whereas a relatively large patient weighing 100 kilograms or more may require dosages provided at the high end of the ranges noted (or more). In some embodiments such a daily dose can be distributed as multiple doses throughout the day. In some of such embodiments the composition of each of such distributed doses can be identical. In other embodiments the composition of such distributed doses can be different, provided the summation of such doses provides the required supplementation.

In an exemplary embodiment human tumor cells (following transplantation into nude mice) are treated with 1 gram per day of the nutritional supplement, radiotherapy, or 1 gram per day of the nutritional supplement and chemotherapy. The mice are weighed during treatment to characterize side effects such as nausea and loss of appetite. After several weeks the mice are sacrificed and the tumor characterized. Tumor volume is determined, and the impact of therapy on organ and muscle volume is determined. The degree of neutropenia is also characterized. A typical protocol is shown in Table 2.

TABLE 2

| | | | Sacrifice (21$^{th}$ day) |
|---|---|---|---|
| 1 | C | Control | N = 6 |
| 2 | T | Tumor | N = 6 |
| 3 | PTN | Tumor + Nutrawell (−7 day start) | N = 6 |
| 4 | TN | Tumor + Nutrawell (0 day start) | N = 6 |
| 5 | TR | Tumor + Radiotherapy (3 Gy × 3) | N = 6 |
| 6 | PTRN | Tumor + Radiotherapy (3 Gy × 3) + Nutrawell (−7 day start) | N = 6 |
| 7 | TRN | Tumor + Radiotherapy (3 Gy × 3) + Nutrawell (0 day start) | N = 6 |

Body Weight/Wasting

Figure 2A:
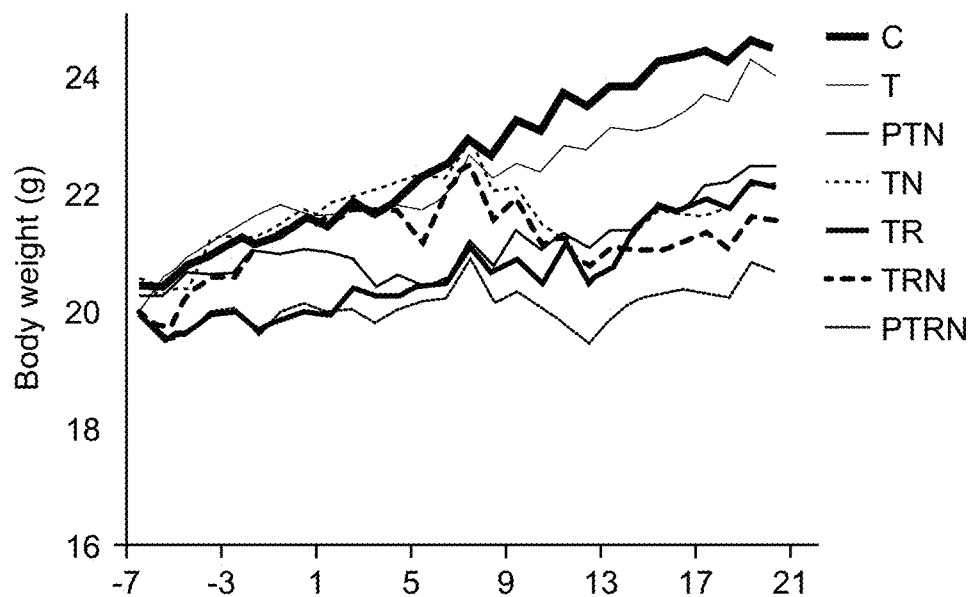
FIGS. 2A and 2B.
Figure 2B:
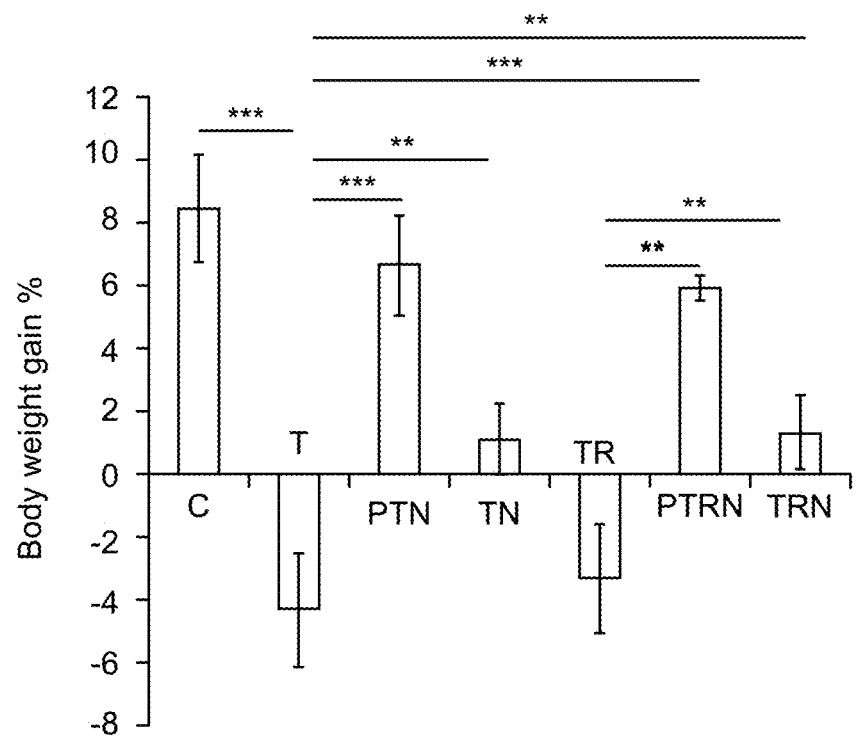

A typical treatment schedule is depicted schematically in FIG. 1. Some subjects received treatment with a supplement containing fish oil and selenium (PTN, PTRN) prior to tumor cell implantation, with a portion of these (PTRN) receiving radiotherapy. Other subject started treatment with such a supplement at the time of tumor cell implantation (TN, TRN), with some of these receiving radiotherapy (TRN). Results of body weight studies compared to control subjects (C) and subjects implanted with tumor cells and otherwise untreated (T) are shown in FIGS. 2A and 2B. As shown, mice receiving both radiotherapy and the supplement containing fish oil and selenium gained weight at a significantly greater rate than those receiving only radiotherapy, indicating a reduction in side effects normally associated with this treatment mode. Pre-treatment with a nutritional supplement containing fish oil and selenium had a particularly pronounced effect.

Tumor Size

Figure 3A:
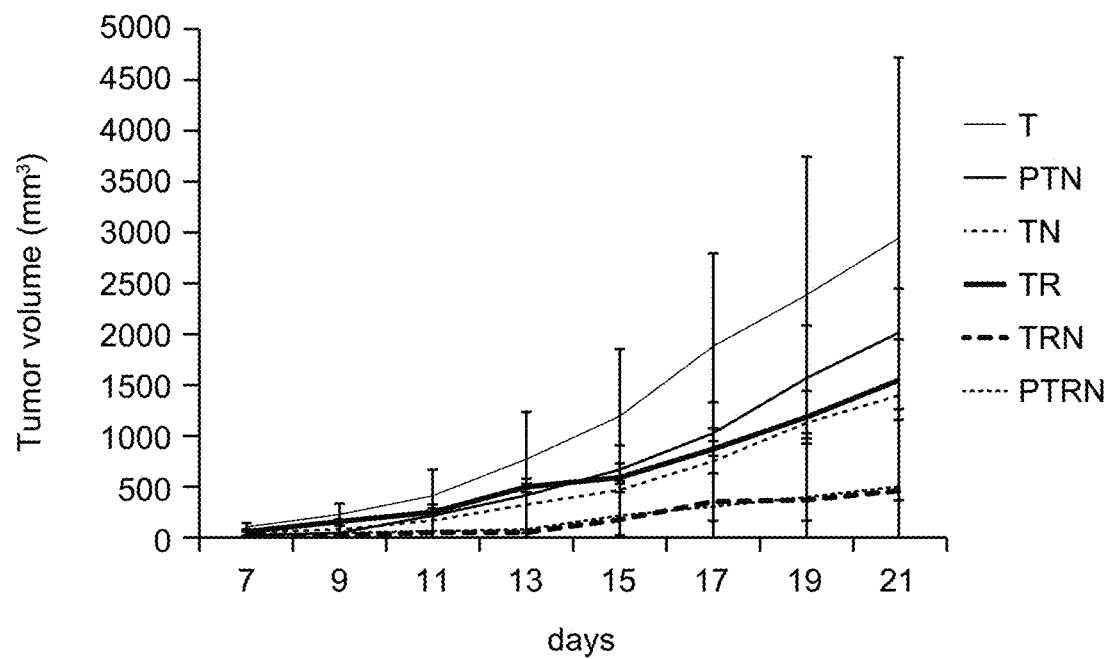
FIGS. 3A to 3D.
Figure 3B:
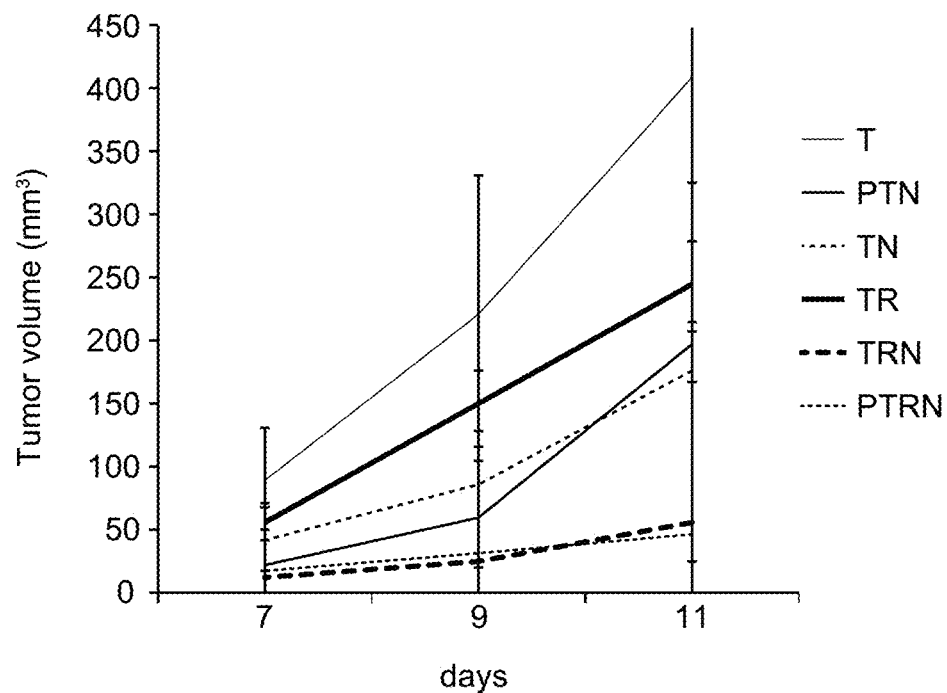
Figure 3C:
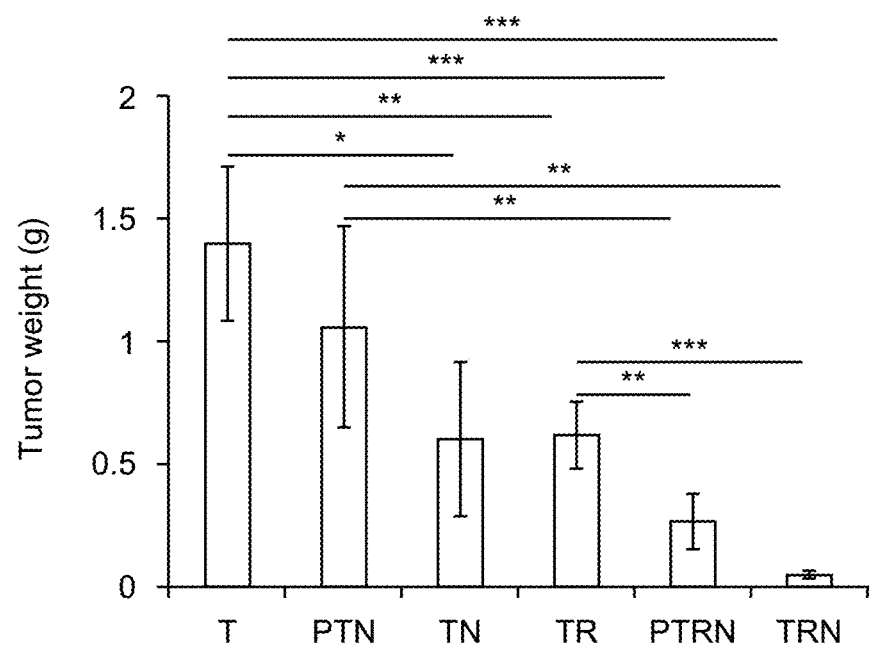
Figure 3D:
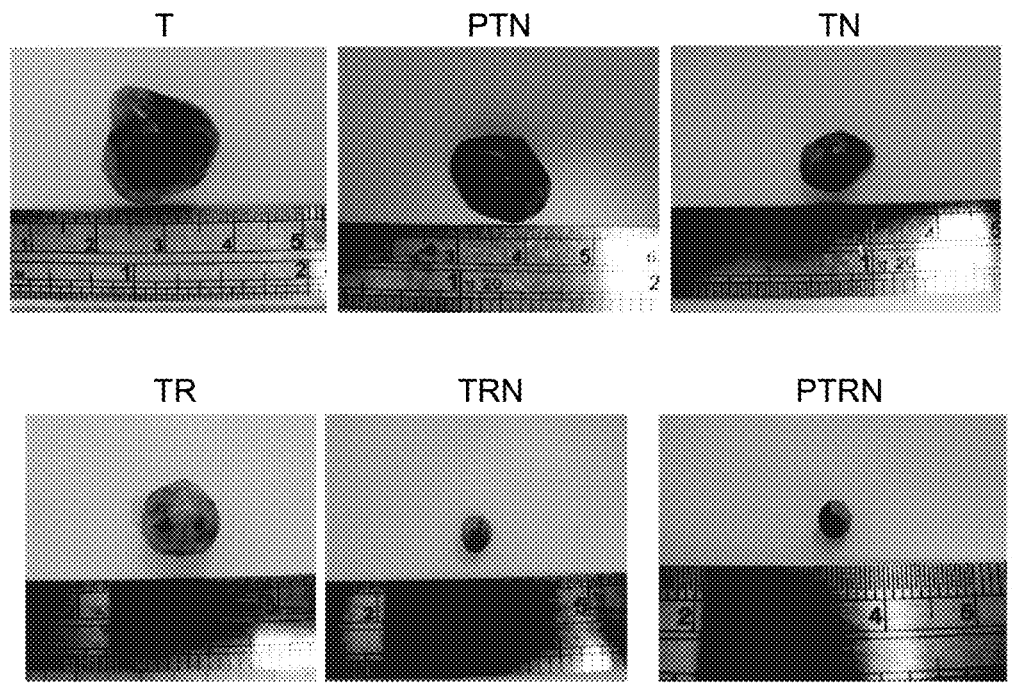

FIGS. 3A to 3D show typical synergistic effects on tumor volume and weight of co-treatment with radiotherapy and a supplement containing fish oil and selenium for similar treatment groups in a murine model of human cancer. FIG. 3A shows the effect of various treatment protocols on tumor volume over the course of 3 weeks, with FIG. 3B providing a scaled view of the effect over the initial 11 days. As shown, treatment with a supplement containing fish oil and selenium alone provides an approximately 60% reduction in tumor volume. Treatment with radiation alone provides a similar reduction in tumor volume. In the absence of a synergistic effect one would therefore anticipate a reduction in tumor volume to approximately 25% of that of the untreated tumor. Surprisingly, what is observed is a greater than 90% reduction in tumor volume to approximately 7% of the untreated tumor-indicative of a significant synergistic effect. FIG. 3C shows that similar effects are found when tumor weight is characterized. FIG. 3D shows photographs typical examples of tumors excised from test animals following treatment; the effects of cotherapy with a nutritional supplement containing fish oil and selenium with radiotherapy is readily apparent on visual inspection. As such, it is apparent that cotherapy with a supplement containing fish oil and selenium and radiotherapy can provide a synergistic effect in reducing tumor volume and/or mass.

Muscle Wasting

Figure 4A:
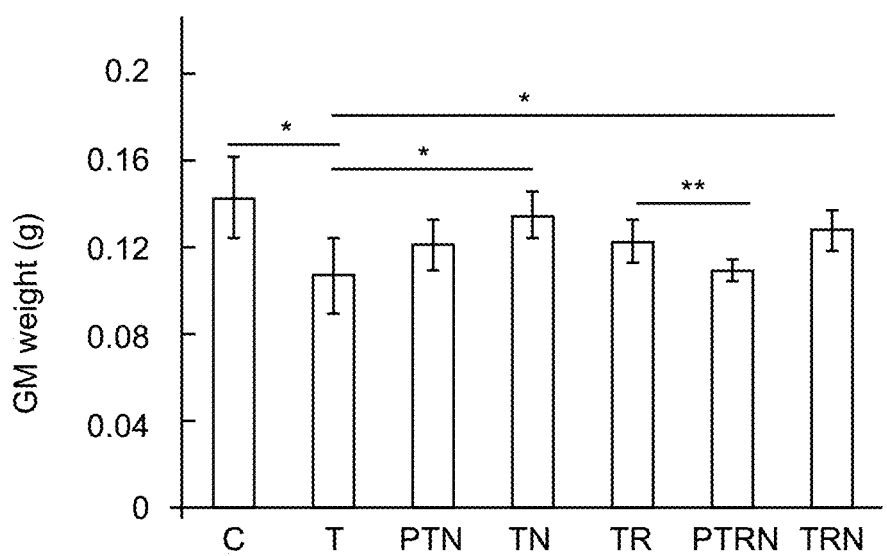
FIGS. 4A to 4G.
Figure 4B:
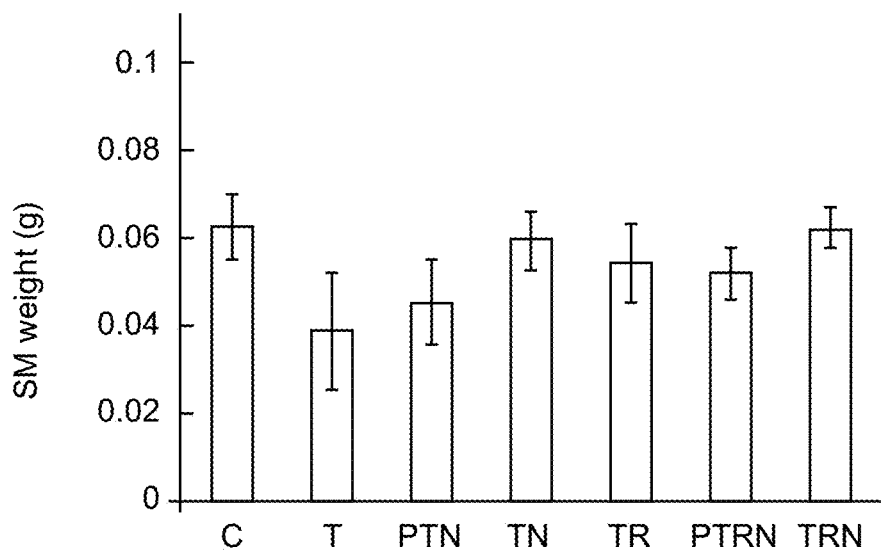

Side effects of radiotherapy go beyond loss of appetite and weight loss, and can include damage to internal organs, loss of muscle mass, anemia, neutropenia, reduction in kidney function, etc. To determine the protective effects of cotherapy with a supplement containing fish oil and selenium in regards to such side effects on muscle mass and organ weight of treated mice were also characterized following therapy. The results are shown in FIGS. 4A to 4E. FIGS. 4A and 4B show the effects of treatment with a supplement containing fish oil and selenium, radiotherapy, and cotherapy with radiotherapy using such a supplement (with and without supplement pre-treatment) on the weight of gastrocnemius muscle and soleus muscle (respectively), with test groups designated as described above. As shown, cotherapy with such a supplement and radiotherapy provides almost complete retention of muscle weight.

Metastasis

Figure 4C:
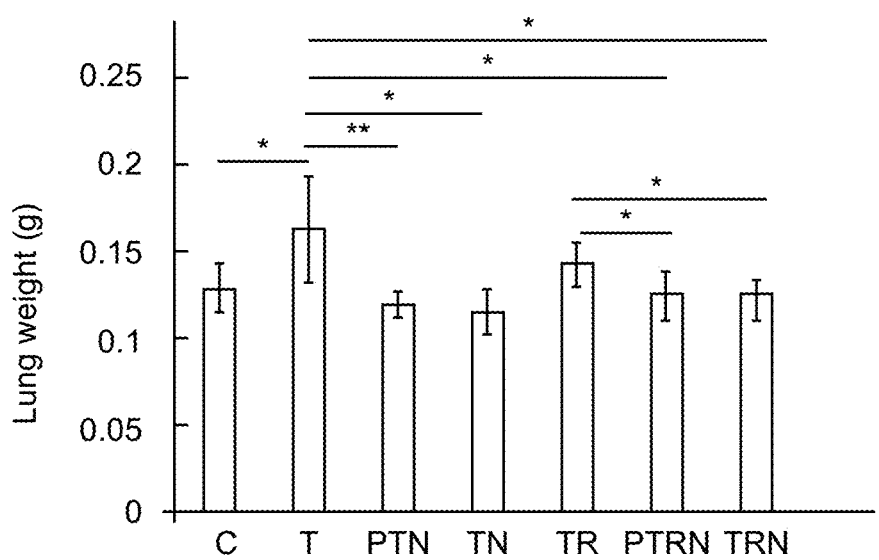
Figure 4D:
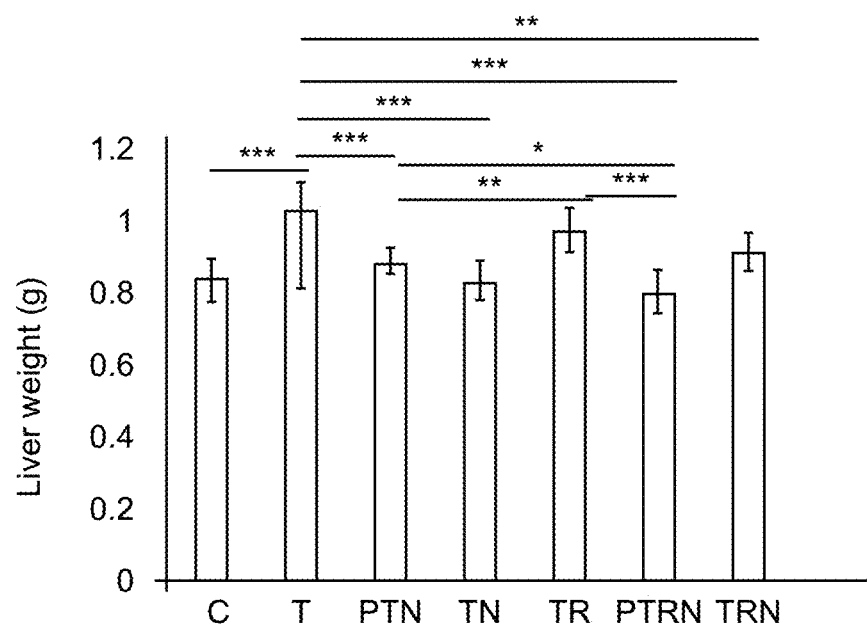
Figure 4E:
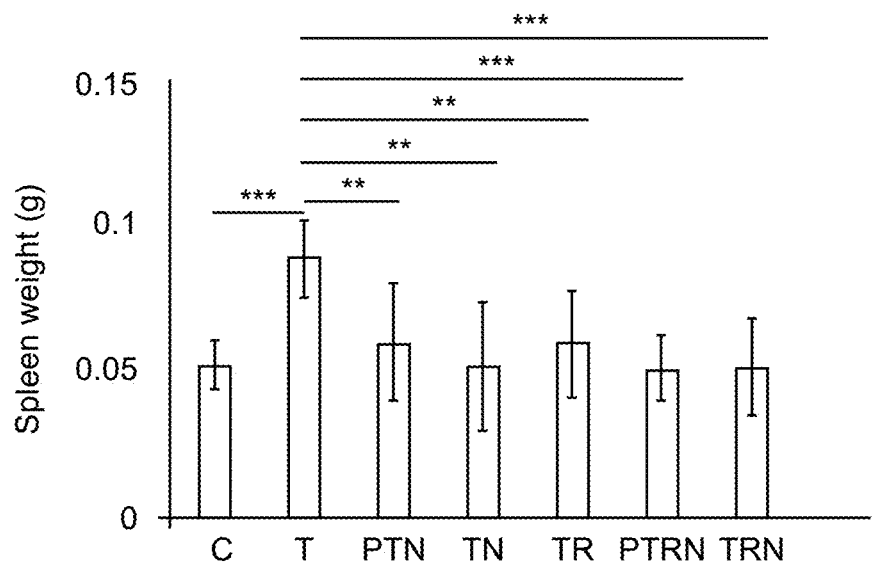

FIGS. 4C, 4D, and 4E show the effects of treatment as described above on the weight lungs inclusive of any metastatic tumors (FIG. 4C), livers inclusive of any metastatic tumors (FIG. 4D), and spleens inclusive of any metastatic tumors (FIG. 4E). As shown lack of treatment leads to an increase in weight, due at least in part to the presence of metastatic tumors. This increase is not entirely mitigated by radiotherapy alone (TR), however subjects receiving treatment with a supplement containing fish oil and selenium had organ weights similar to those of control subjects, both with and without cotherapy with radiotherapy.

Figure 4F:
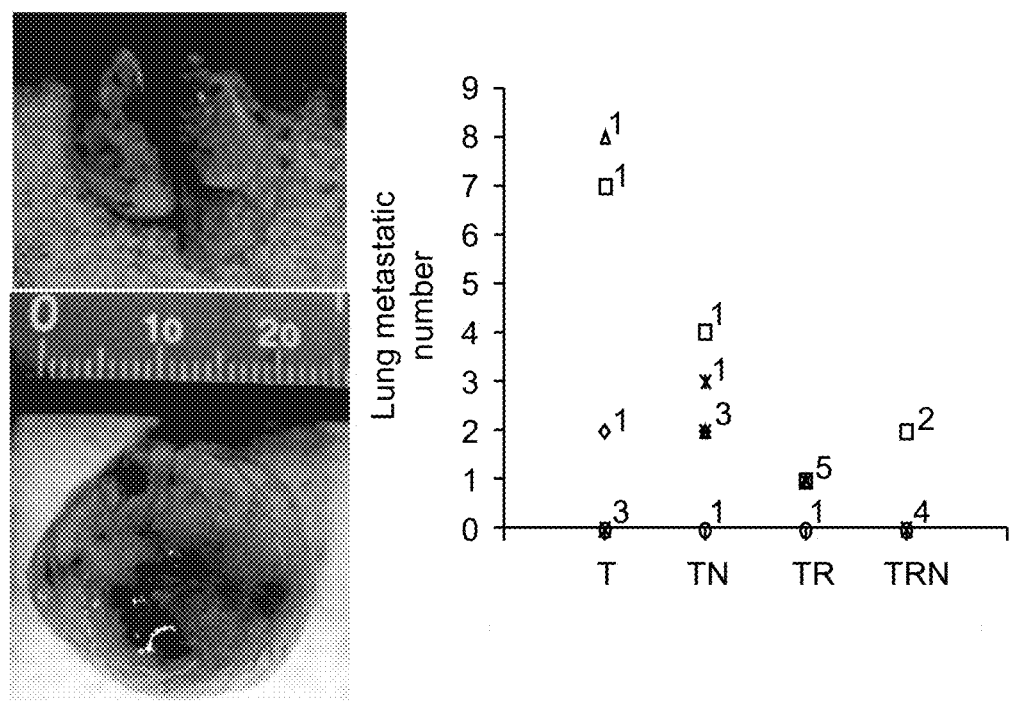

Similarly, quantitation of metastatic sites within the lungs of animal models of human disease treated with a nutritional supplement containing fish oil and selenium and/or radiotherapy. Typical metastatic sites are shown in the photographs in the left panel of FIG. 4F, and enumerated in a histogram in the right panel. As shown, treatment with either such a supplement (TN) or radiotherapy (TR) reduced the number of metastatic sites to some extent, however treatment with both the supplement and radiotherapy (TRN) resulted in a complete lack of apparent metastatic sites in most subjects.

Figure 4G:
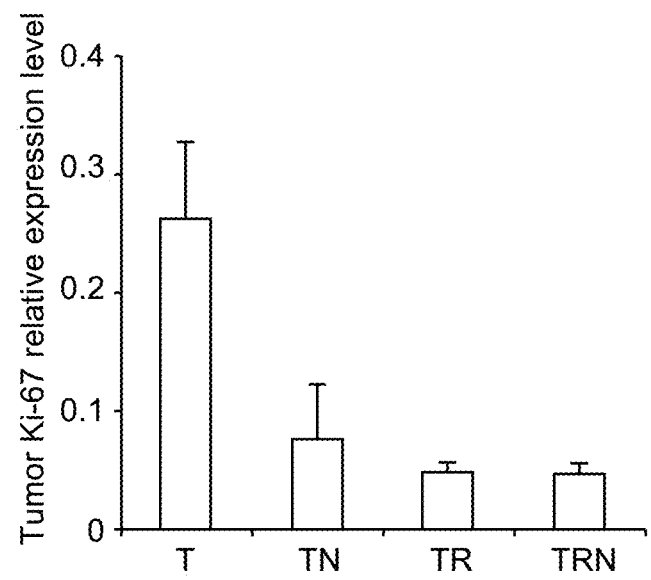
Figure 4G:
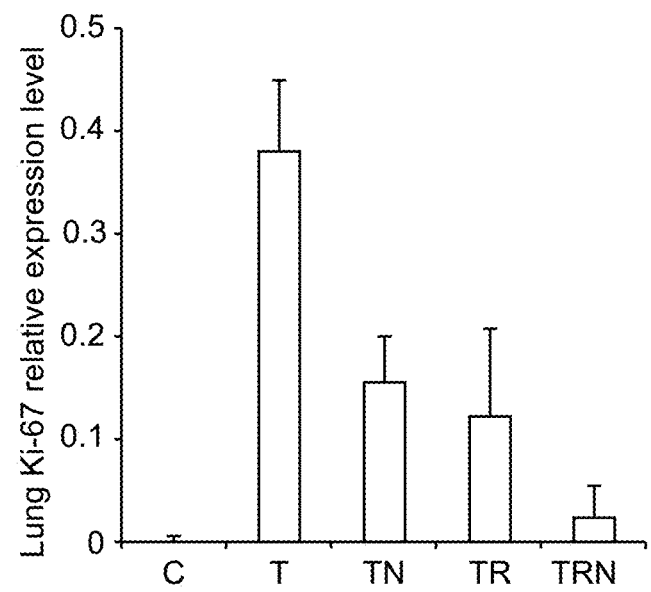

Without wishing to be bound by theory, the Inventor believes that this effect on metastasis (and also on tumor size and mass, as shown above) can be due to a synergistic effect provided by the use of a nutritional supplement containing fish oil and selenium in combination with radiotherapy on tumor cell proliferation. As shown in FIG. 4G, the expression of the proliferation marker Ki-67 is suppressed in the primary tumor site on treatment with either a supplement containing fish oil and selenium (TN), on treatment with radiotherapy (TR), or treatment using both modes (TRN). Metastatic sites (right panel) show a related trend, with treatment with the nutritional supplement or radiotherapy alone resulting in a moderate reduction in the expression of this proliferation marker, but surprisingly showing a synergistic effect in reducing expression of Ki-67 in metastatic sites. This indicates that use of a supplement containing fish oil and selenium can reduce tumor metastasis, including metastasis that is not prevented by radiotherapy, and can do so in a synergistic manner.

Neutropenia/Anemia

Anemia and neutropenia are often found in cancer and as side effects of radiotherapy, due at least in part to suppression of bone marrow activity. The effects of cotherapy with a supplement containing fish oil and selenium on various blood cell populations are shown in FIGS. 5A to 5E. FIG. 5B shows the effects of a nutritional supplement containing fish oil and selenium, radiotherapy, and cotherapy with such a supplement and radiotherapy on white blood cells as shown in FIG. 5B, and lymphocytes as shown in FIG. 5C. This indicates that a nutritional supplement containing fish oil and selenium can be useful to improve red blood cell, granulocyte, white blood cell, and/or lymphocyte suppression resulting from the presence of a tumor and from radiotherapy utilized in the treatment of such tumors.

Figure 5A:
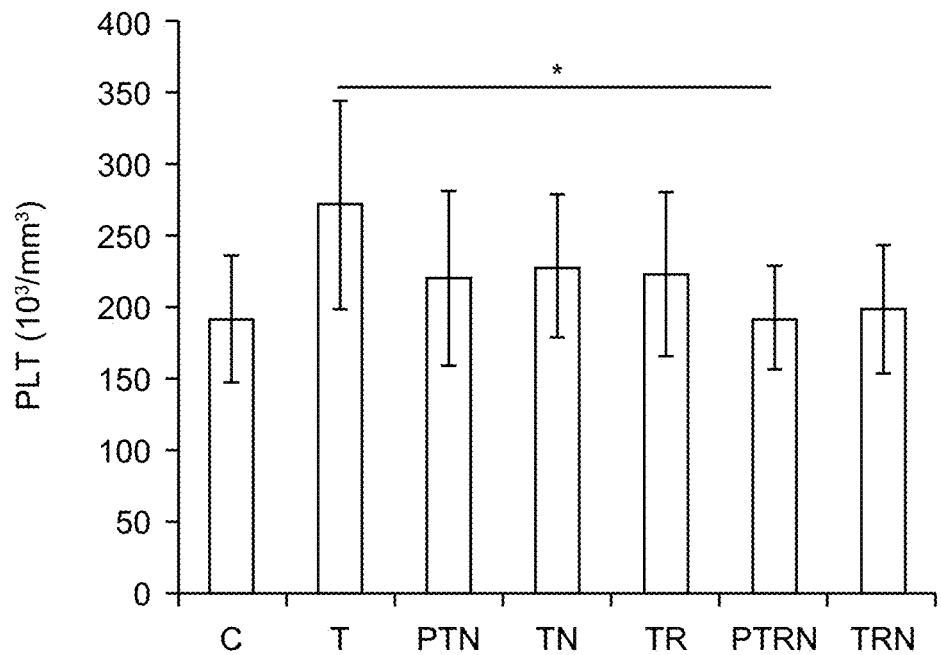
FIGS. 5A to 5E.
Figure 5B:
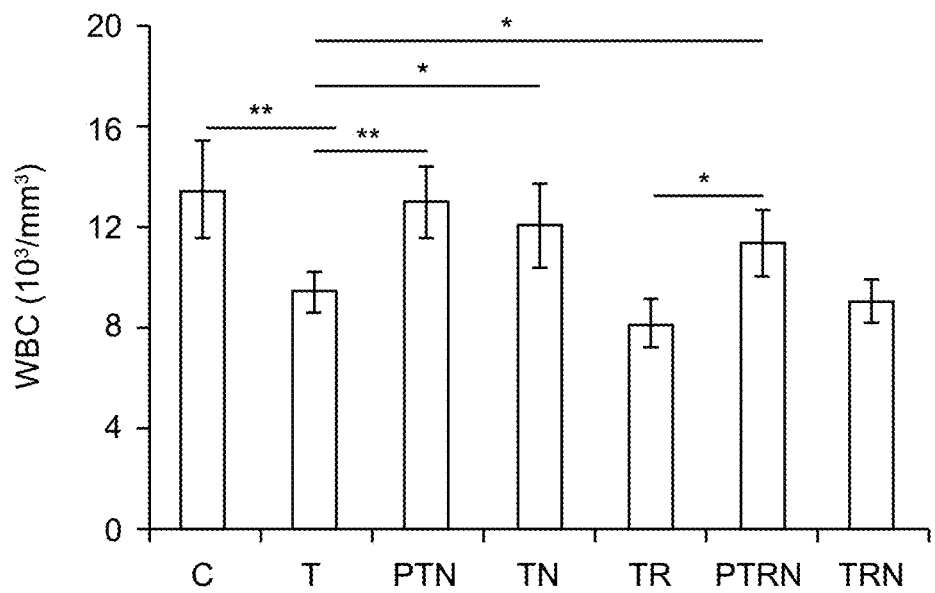
Figure 5C:
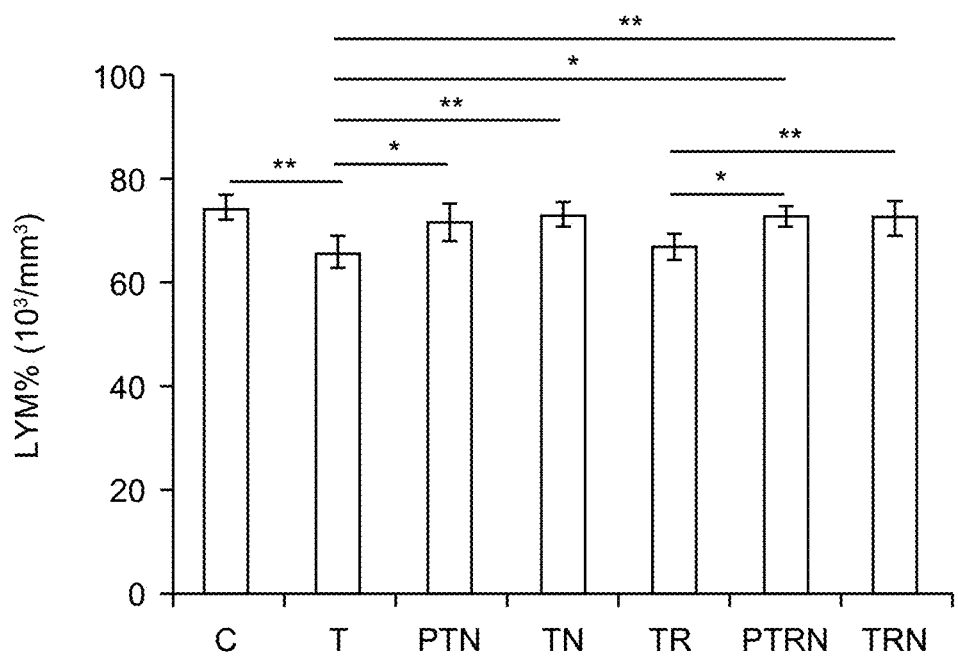
Figure 5D:
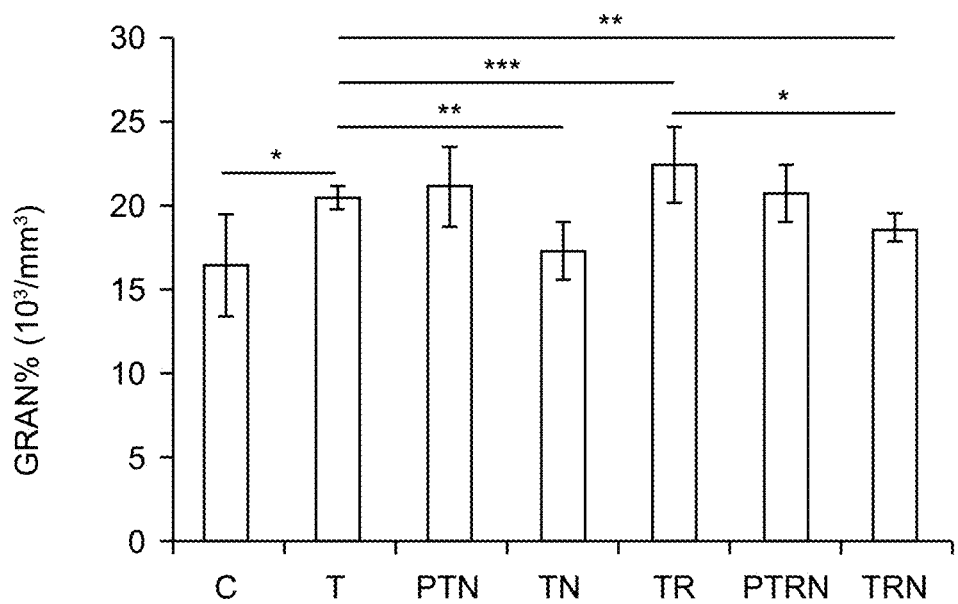
Figure 5E:
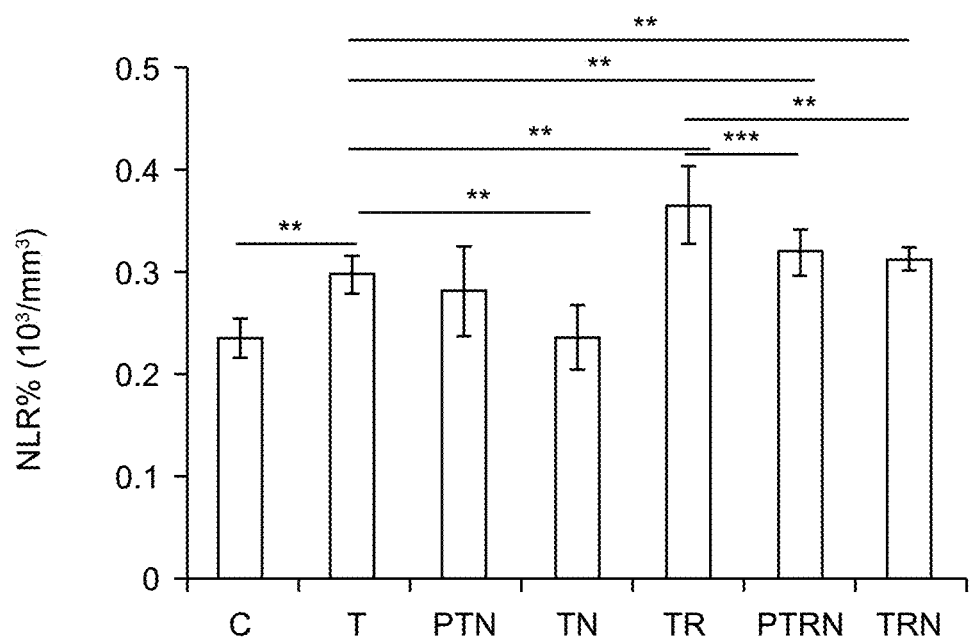

As shown in FIG. 5A, platelets were found to be elevated in untreated animals bearing tumors (T). Platelet concentrations were reduced by treatment with either a supplement containing fish oil and selenium or radiotherapy, but were most pronounced in animals receiving cotherapy with such a supplement and radiotherapy. This effect was particularly pronounced in subjects receiving pre-treatment with a supplement containing fish oil and selenium, which reduced platelet concentrations to the values found for control animals. Granulocyte concentrations were similarly elevated in untreated tumor bearing animals (as shown in FIG. 5D), and were further elevated in such animals receiving only radiotherapy. Cotherapy with a nutritional supplement containing fish oil and selenium and radiotherapy, was found to reduce this effect. As shown in FIG. 5E, tumor bearing animals show an elevated neutrophil/lymphocyte ratio (NLR) relative to control animals, which is even more elevated in similar subjects receiving only radiotherapy. Treatment with a supplement containing fish oil and selenium was found to be effective in shifting this ratio towards a more normal value, both as a monotherapy and as a part of cotherapy with radiotherapy. This indicates that a nutritional supplement containing fish oil and selenium can be useful in reducing platelet concentration, granulocyte concentration, and/or neutrophil/lymphocyte ratios that are elevated due to the presence of a tumor and due to radiotherapy used to treat such a tumor.

Serum Proteins

Figure 6A:
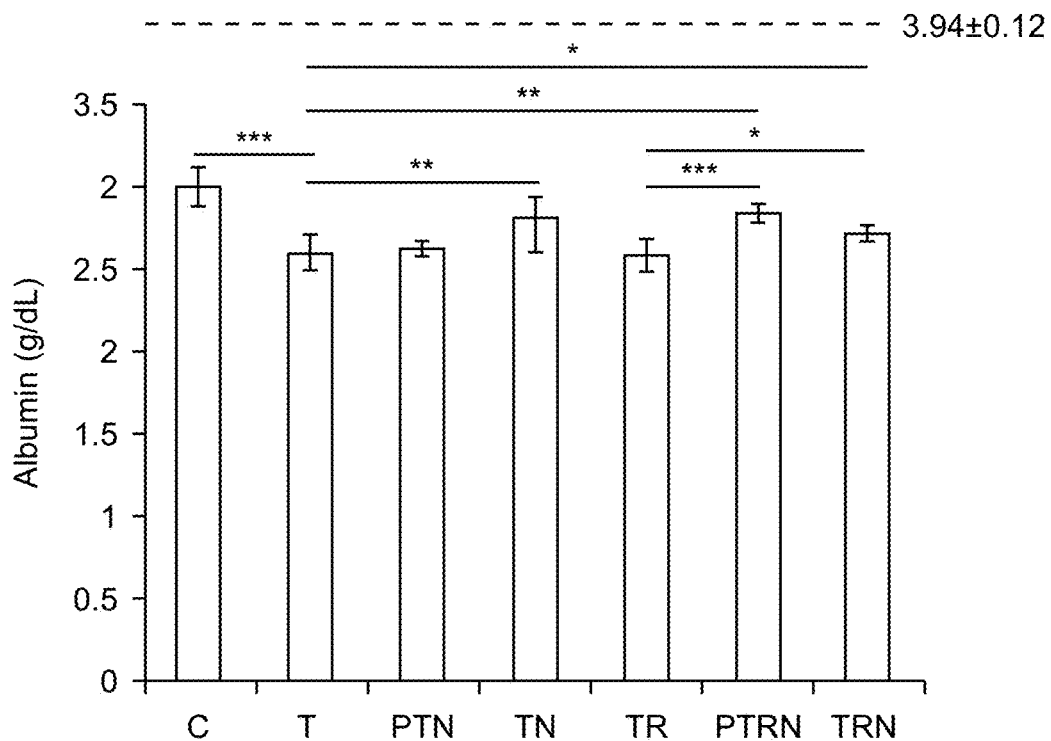
FIGS. 6A and 6B.
Figure 6B:
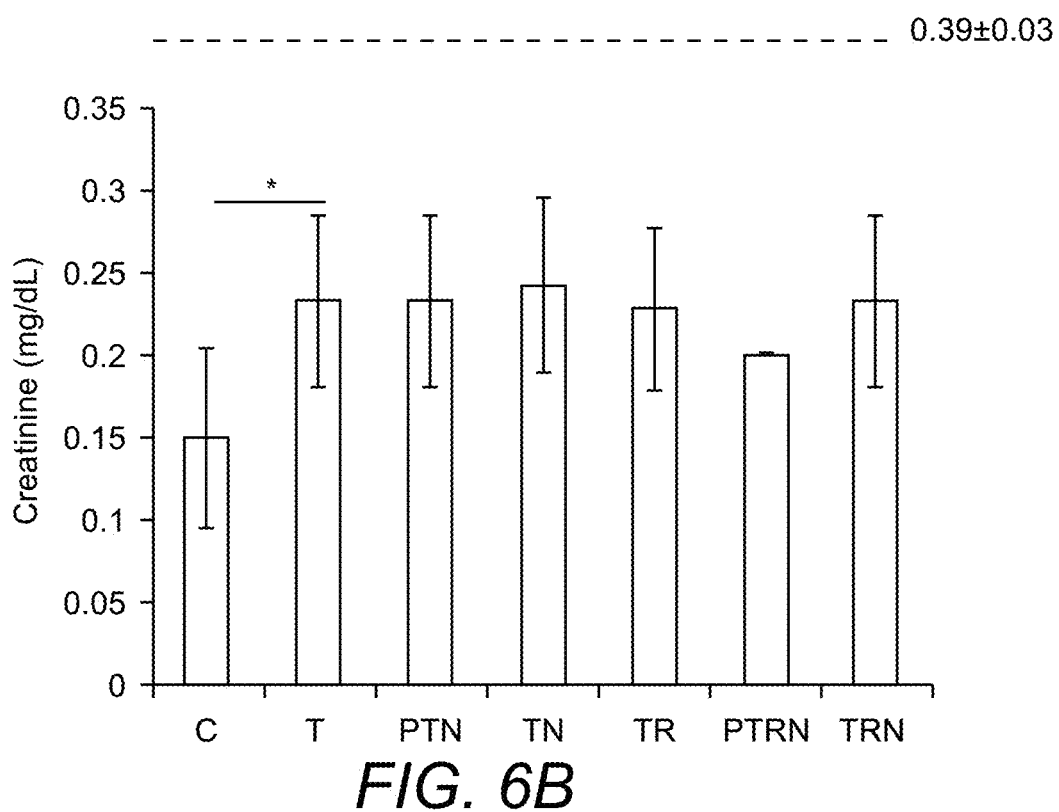

The effects of cotherapy with a supplement containing fish oil and selenium on various serum biochemistry markers, which provide information regarding kidney function, liver function, and/or nutritional status are shown in FIGS. 6A and 6B. FIG. 6A shows the effects of a nutritional supplement containing fish oil and selenium, radiotherapy, and cotherapy with such a supplement and radiotherapy on an animal tumor model. As shown, serum albumin concentration (an indicator of nutritional status) is reduced in untreated tumor-bearing animals, and is only slightly improved by radiotherapy alone. Treatment with a nutritional supplement containing fish oil and selenium, either as a monotherapy or as cotherapy with radiotherapy, improves serum albumin concentration—particularly when such a supplement is provided as a pretreatment. This is improved by cotherapy with a nutritional supplement containing fish oil and selenium. This indicates that treatment with a nutritional supplement containing fish oil and selenium, either as a monotherapy or as cotherapy with radiotherapy, can improve the nutritional status of tumor-bearing subjects.

FIG. 6B shows the results of similar studies where serum creatinine (a measure of kidney function) is characterized. As shown, untreated tumor bearing subjects shown elevated creatinine concentrations indicative of kidney damage. This is marginally improved by radiotherapy alone. Cotherapy with a nutritional supplement containing fish oil and selenium and radiotherapy, however, shows a synergistic effect in reducing serum creatinine concentrations—particularly when such a nutritional supplement is provided as a pretreatment.

Cytokines

Figure 7A:
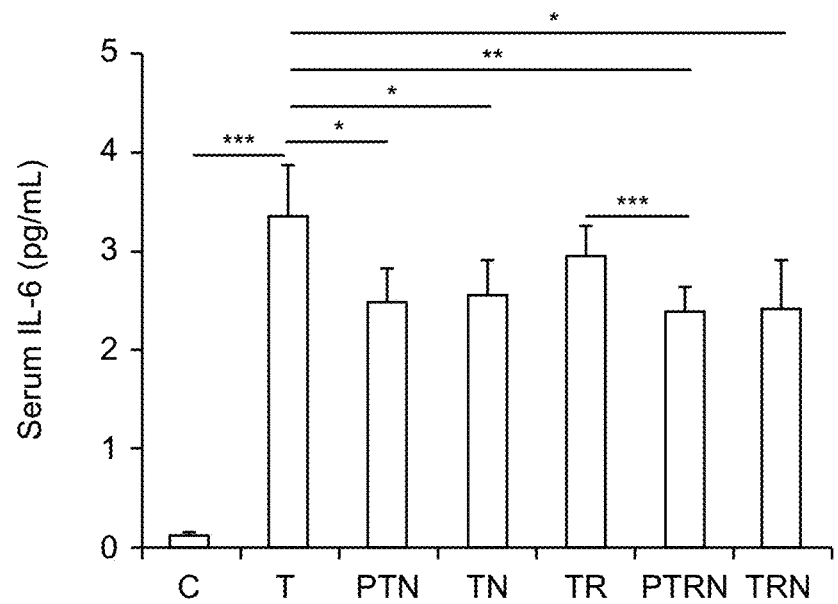
FIGS. 7A and 7B.
Figure 7B:
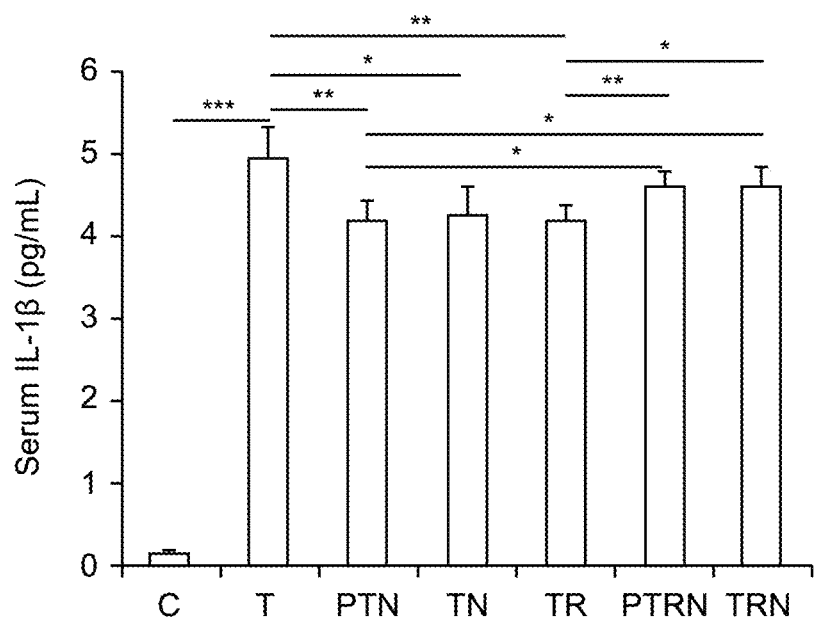

The growth and spread of tumors is associated with inflammation, as is the application of radiotherapy. Surprisingly, Inventors have found that cotherapy with a supplement containing fish oil and selenium is effective in reducing the concentration of pro-inflammatory cytokines, indicating that such co-treatment is effective in reducing inflammation associated with tumors, and with radiotherapy of tumors. The effects of NutraWell supplement on serum concentrations of pro-inflammatory cytokines is shown in FIGS. 7A and 7B. FIG. 7A shows the concentration of IL-6 in control animals, untreated tumor-bearing animals, and tumor bearing animals treated with a nutritional supplement containing fish oil and selenium, radiotherapy, or such a supplement and radiotherapy in combination. As shown, untreated tumor-bearing animals show a large increase in serum IL-6 concentration. This is only somewhat reduced by radiotherapy. Use of a nutritional supplement containing fish oil and selenium, either as a monotherapy or as cotherapy with radiotherapy, was found to reduce serum IL-6 concentrations in tumor-bearing animals. FIG. 7B shows the results of similar studies of IL-1$\beta$. The results with IL-1$\beta$ are similar to those found for IL-6. This indicates that a nutritional supplement containing fish oil and selenium can effectively reduce serum concentrations of inflammation-associated cytokines in tumor-bearing subjects, either as a monotherapy or as cotherapy with radiotherapy. The Inventor believes that such reduction is accompanied by a reduction in inflammation in such animals.

Tumor Gene Expression

Figure 8A:
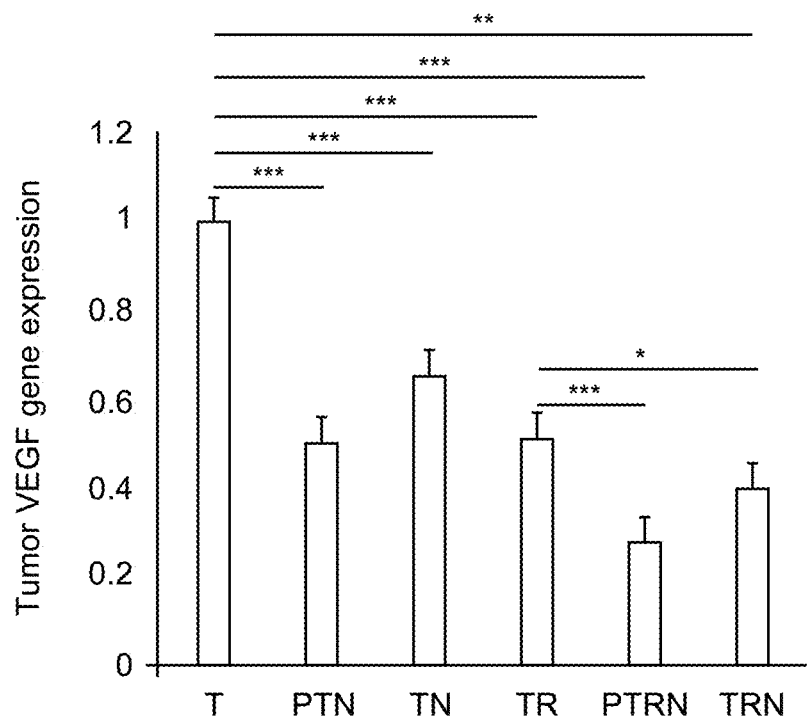
FIGS. 8A to 8G.

Surprisingly, Inventors have also found that treatment with a nutritional supplement containing fish oil and selenium can modify gene expression in tumor cells in vivo, and can provide a synergistic effect to such changes in gene expression resulting from radiotherapy. In some embodiments the genes are related to cytokines and/or are related to apoptosis. Examples of the effect of radiotherapy, treatment with a nutritional supplement containing fish oil and selenium, and cotherapy with radiotherapy on gene expression in implanted tumor cells in vivo are shown in FIG. 8A to 8G. FIG. 8A shows the results of such treatments on the expression of VEGF in tumor cells. As shown, monotherapy with a nutritional supplement containing fish oil and selenium and radiotherapy reduced VEGF expression. Cotherapy with a nutritional supplement containing fish oil and selenium and radiotherapy provided dramatically reduced expression of VEGF.

Figure 8B:
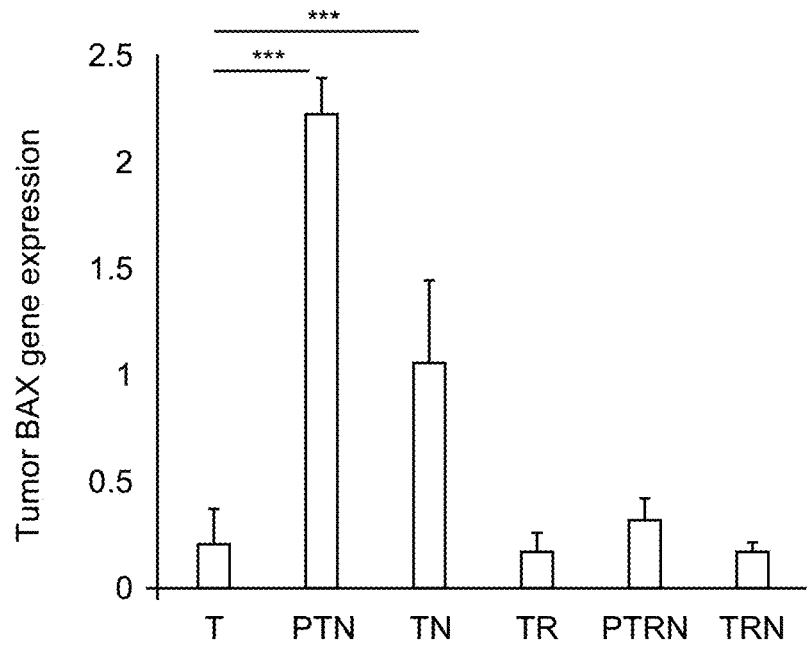
Figure 8C:
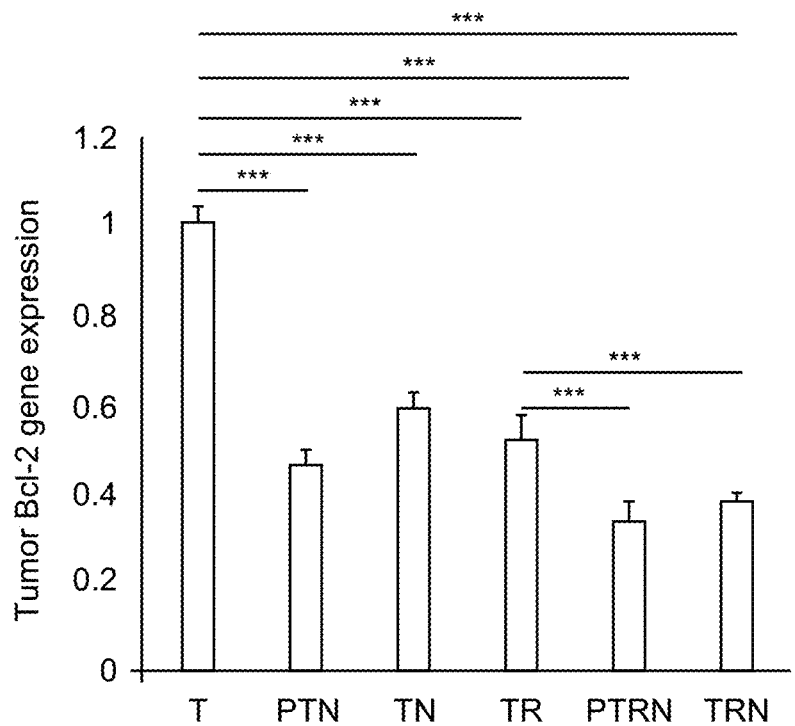
Figure 8D:
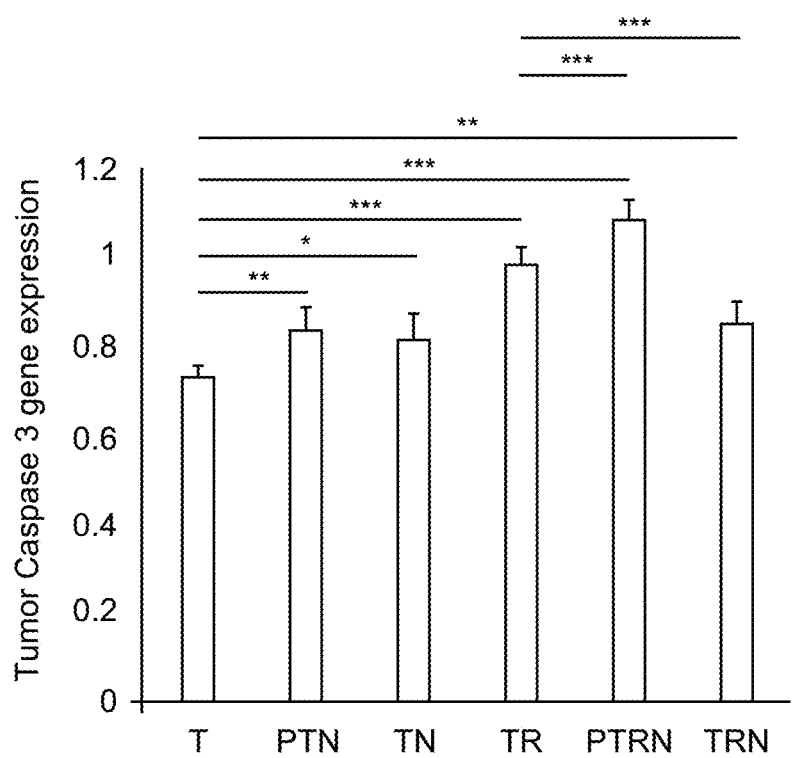
Figure 8E:
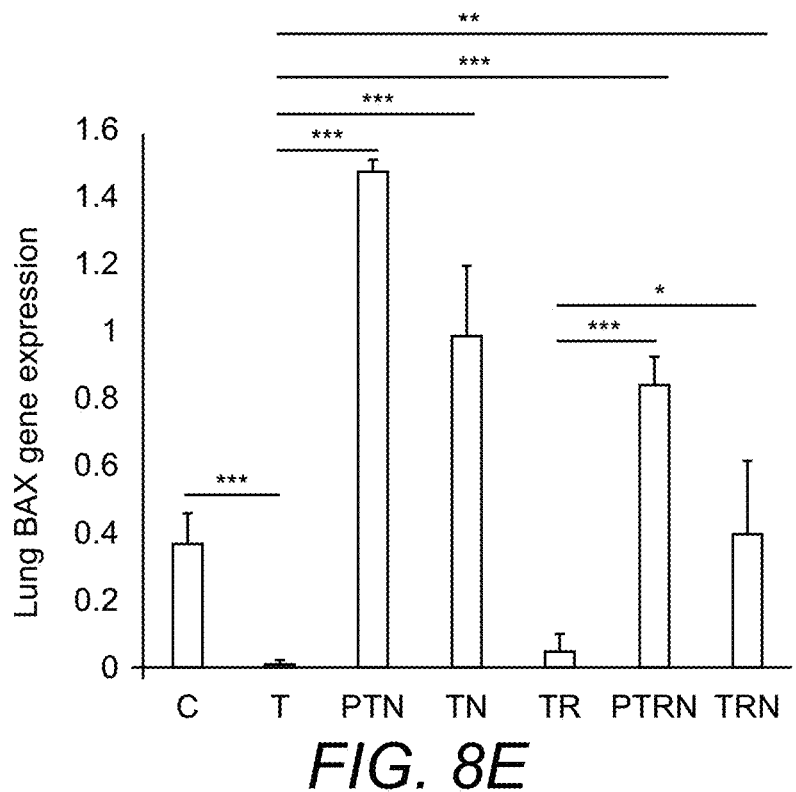
Figure 8F:
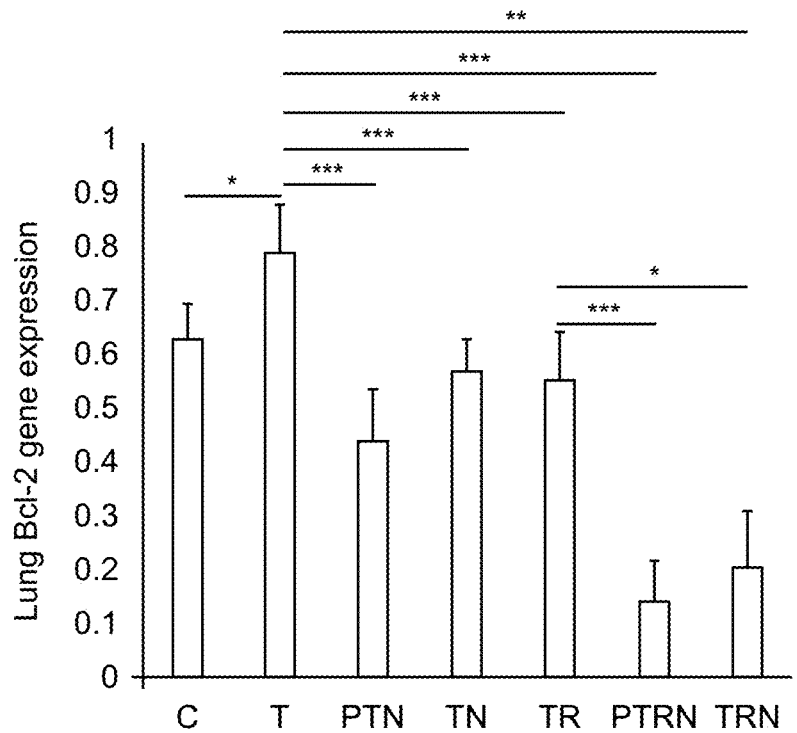
Figure 8G:
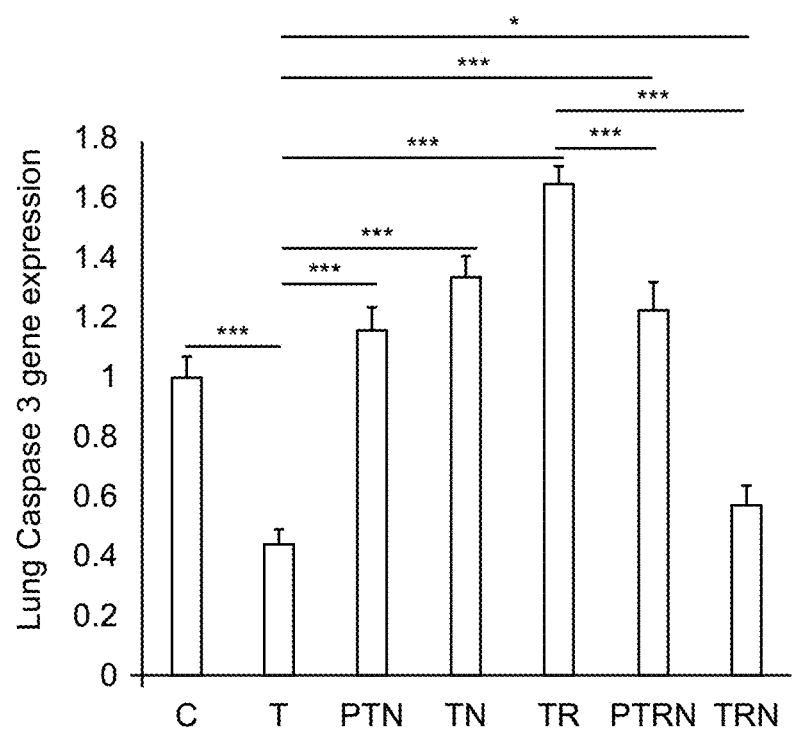

FIGS. 8B and 8D show the effects of treatment with a nutritional supplement containing fish oil and selenium, radiotherapy, and cotherapy with such a supplement and radiotherapy on tumor BAX expression and metastatic (lung) tumor BAX expression, respectively. BAX is considered a marker for apoptosis. As shown, BAX expression in untreated tumor is low, and is not impacted by radiotherapy. Monotherapy with a nutritional supplement containing fish oil and selenium resulted in dramatic increases in BAX expression, and elevated BAX expression when used as cotherapy with radiotherapy (particularly with the supplement was provided as a pretreatment). As shown in FIGS. 8C and 8E, Bcl-2 expression was found to be elevated in tumor cells and metastatic (lung) tumor cells (respectively), and was reduced by either treatment with a nutritional supplement containing fish oil and selenium or radiotherapy as monotherapies. Greater reductions in Bcl-2 expression were found when such a supplement and radiotherapy were used as cotherapies. Expression of caspase 3 (which is associated with apoptosis) is elevated in tumors (FIG. 8D) treated with radiotherapy or with a nutritional supplement containing fish oil and selenium alone, and is also elevated by cotherapy with such a supplement as radiotherapy (particularly when the supplement is provided as a pre-treatment). As shown in FIG. 8F, expression of caspase 3 is reduced in metastatic (lung) tumors relative to lung tissue of control subjects. As shown, caspase 3 expression in such tumors is increased by radiotherapy or treatment with a nutritional supplement containing fish oil and selenium, as well as cotherapy.

Repeated Radiotherapy

Similar studies were performed using modified treatment protocols. One modified treatment protocol utilizing multiple rounds of radiotherapy, as is typical with human radiotherapy, is shown in FIGS. 9A and 9B.

Figures 9A, 9B:
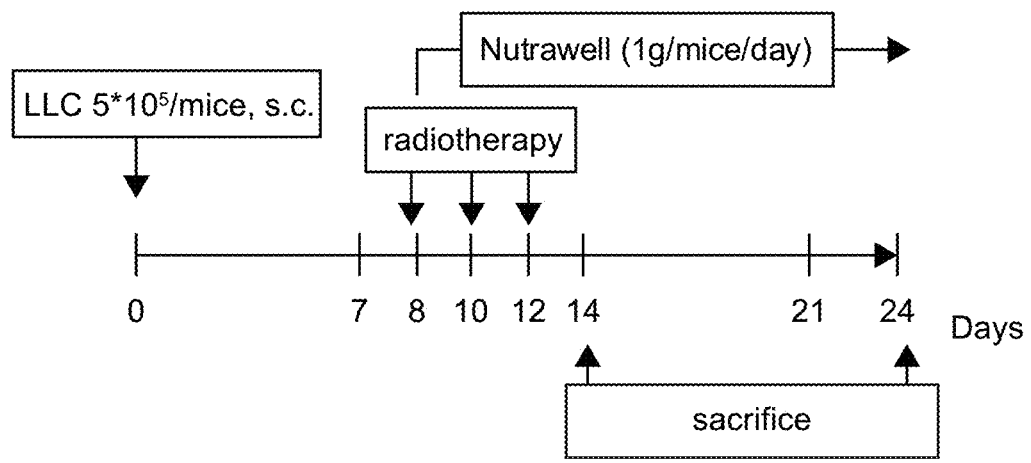
FIGS. 9A and 9B.
Figure 10A:
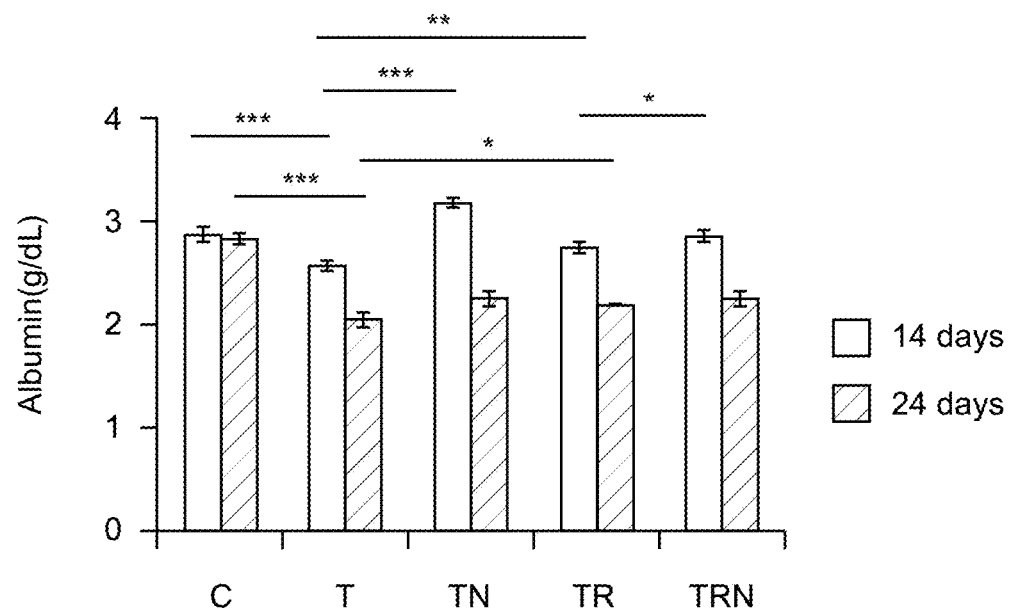
FIGS. 10A to 10C.
Figure 10B:
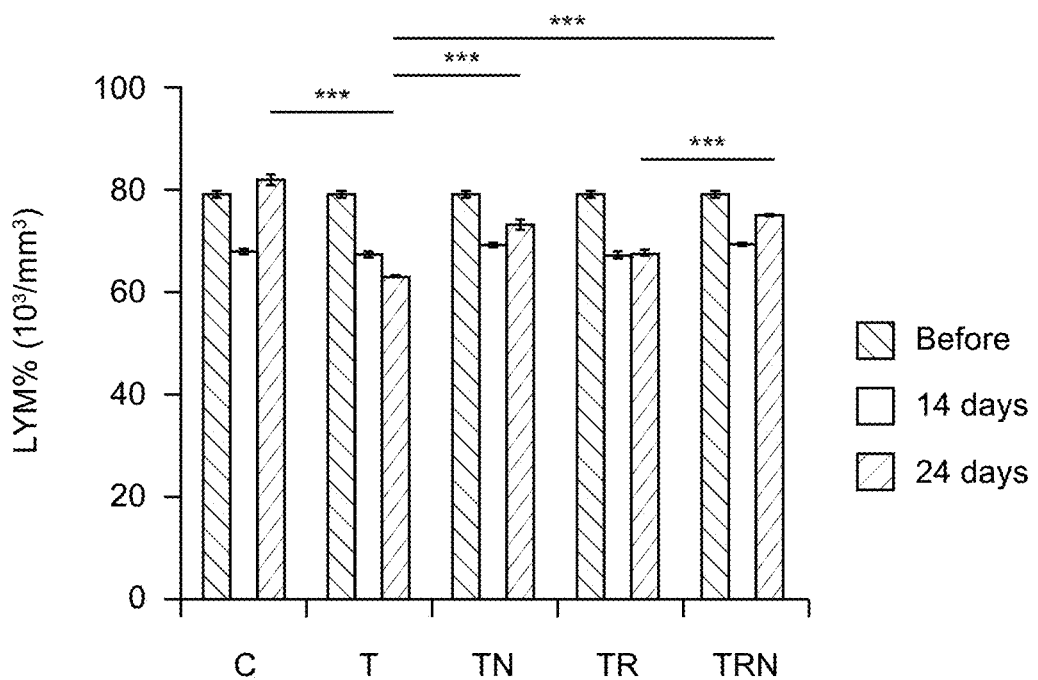
Figure 10C:
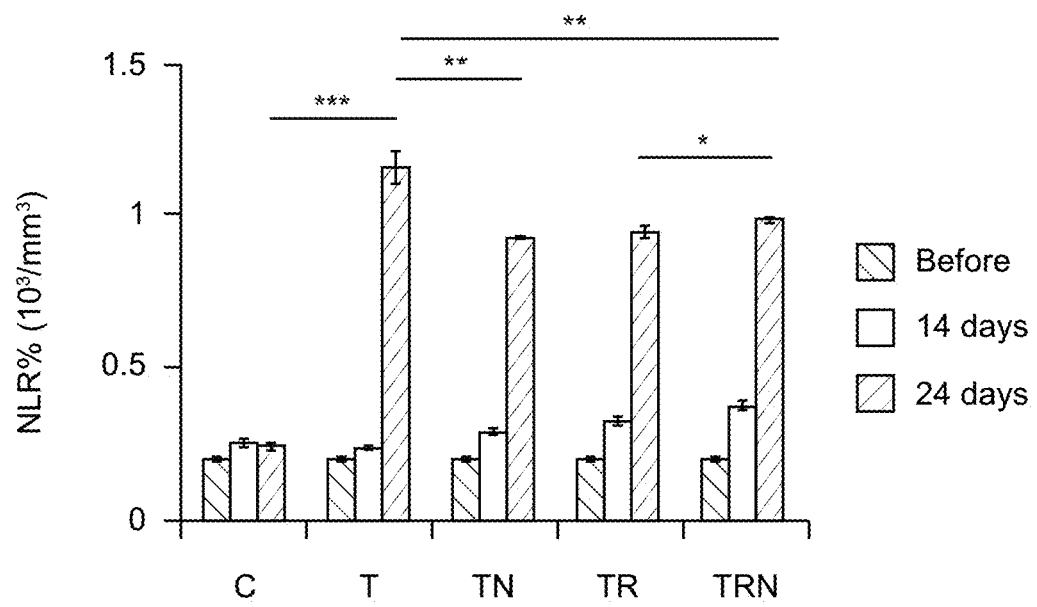

Results from serum albumin and blood cell characterization studies following treatment with NutraWell, radiotherapy, and combined treatment with a nutritional supplement containing fish oil and selenium and radiotherapy using the protocol shown in FIG. 9A are shown in FIGS. 10A to 10C. As shown in FIG. 10A serum albumin concentration is reduced in tumor bearing animals, particularly at later time points. This is improved by treatment with a nutritional supplement containing fish oil and selenium or radiotherapy as monotherapies, and by cotherapy. As shown in FIG. 10B, tumor bearing animals showed suppressed lymphocyte counts relative to control subjects, particularly at later time points. This was only marginally improved by radiotherapy alone, however treatment with a nutritional supplement containing fish oil and selenium (either as a monotherapy or in combination with radiotherapy) was effective in increasing lymphocyte concentration—particularly in later time points. FIG. 10C shows the results of similar studies wherein the neutrophil/lymphocyte ratio (NLR) was characterized. As shown, animals bearing tumors show a dramatic elevation in this value at later time points. This is reduced by treatment with a nutritional supplement containing fish oil and selenium, radiotherapy, and cotherapy with such a supplement and radiotherapy.

Surprisingly, treatment with a nutritional supplement containing fish oil and selenium, radiotherapy, and combined treatment with such a supplement and radiotherapy using the protocol shown in FIG. 9A also has an impact on both expression of tumor cell markers and tumor cell metastasis. In the following studies the tumor cells selected for implantation are derived from a lung tumor and have a strong tendency to metastasize to the lung from the implantation site. FIGS. 11A to 11D show the results of immunocytochemistry studies of different tissues from mice treated with the protocol shown in FIG. 9A. It is notable that NutraWell supplementation alone reduces or eliminates metastasis.

Figure 11A:
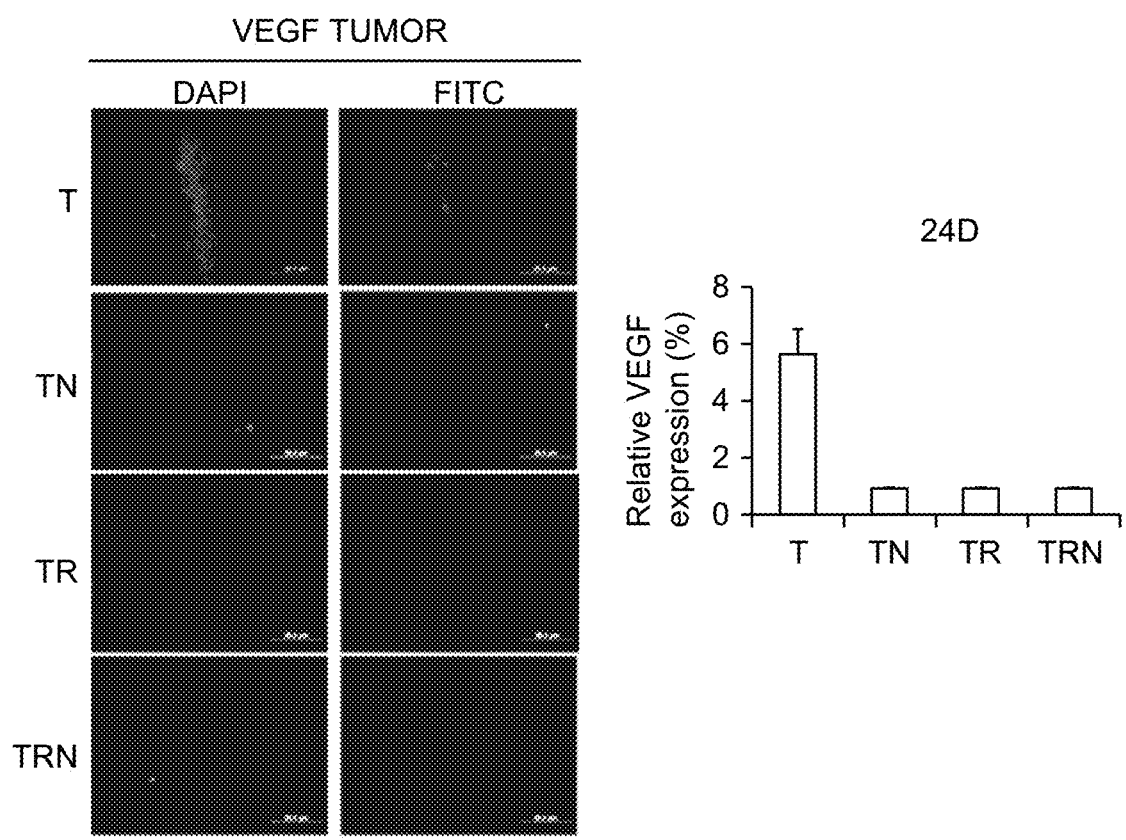
FIG. 11A to 11D.
Figure 11B:
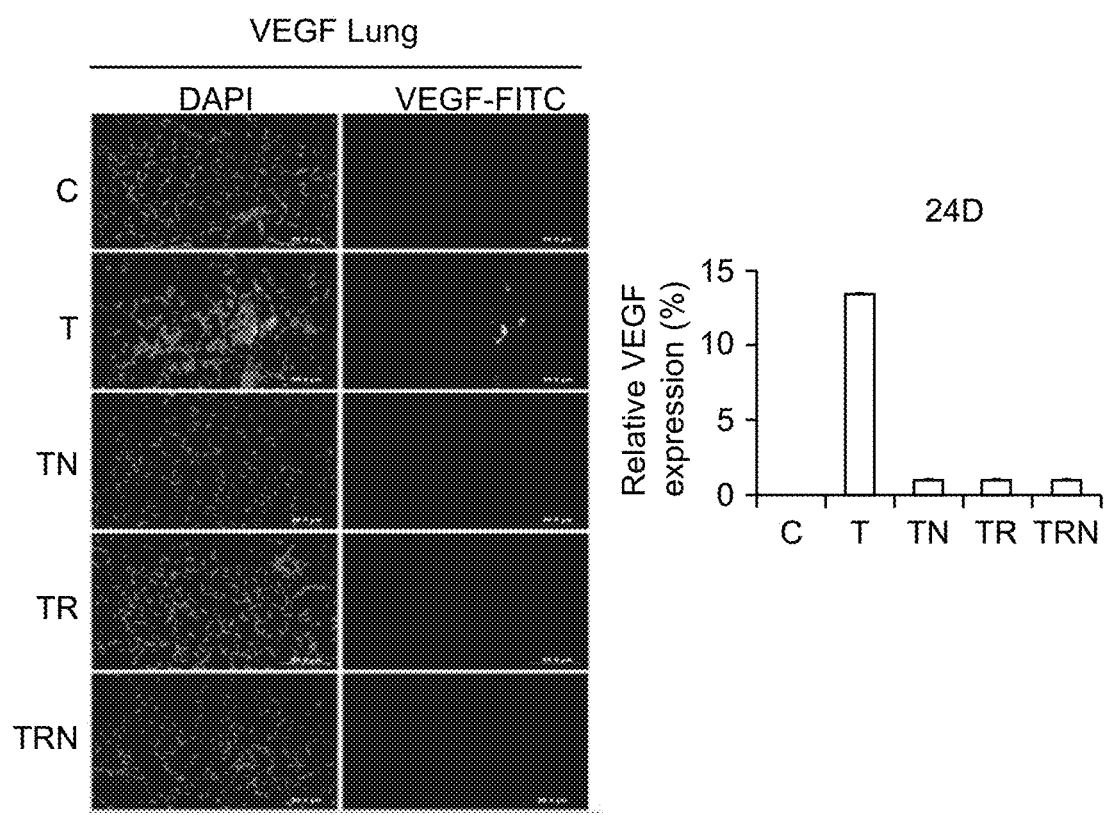

As shown in FIG. 11A, VEGF expression within the tumor of untreated mice (left panel, FITC staining) is evident. Treatment with either a nutritional supplement containing fish oil and selenium or radiotherapy alone dramatically reduced VEGF expression, as does cotherapy. Numerical results are provided in the right panel of FIG. 11A. Similar results are found in tumors that have metastasized to the lungs, as shown in FIG. 11B. As shown, VEGF expression is apparent in untreated metastatic tumors (left panel, FITC staining) and is sharply reduced in animals that received treatment with a nutritional supplement containing fish oil and selenium, radiotherapy, or both. Numerical results of these studies are provided in the right panel of FIG. 11B.

Figure 11C:
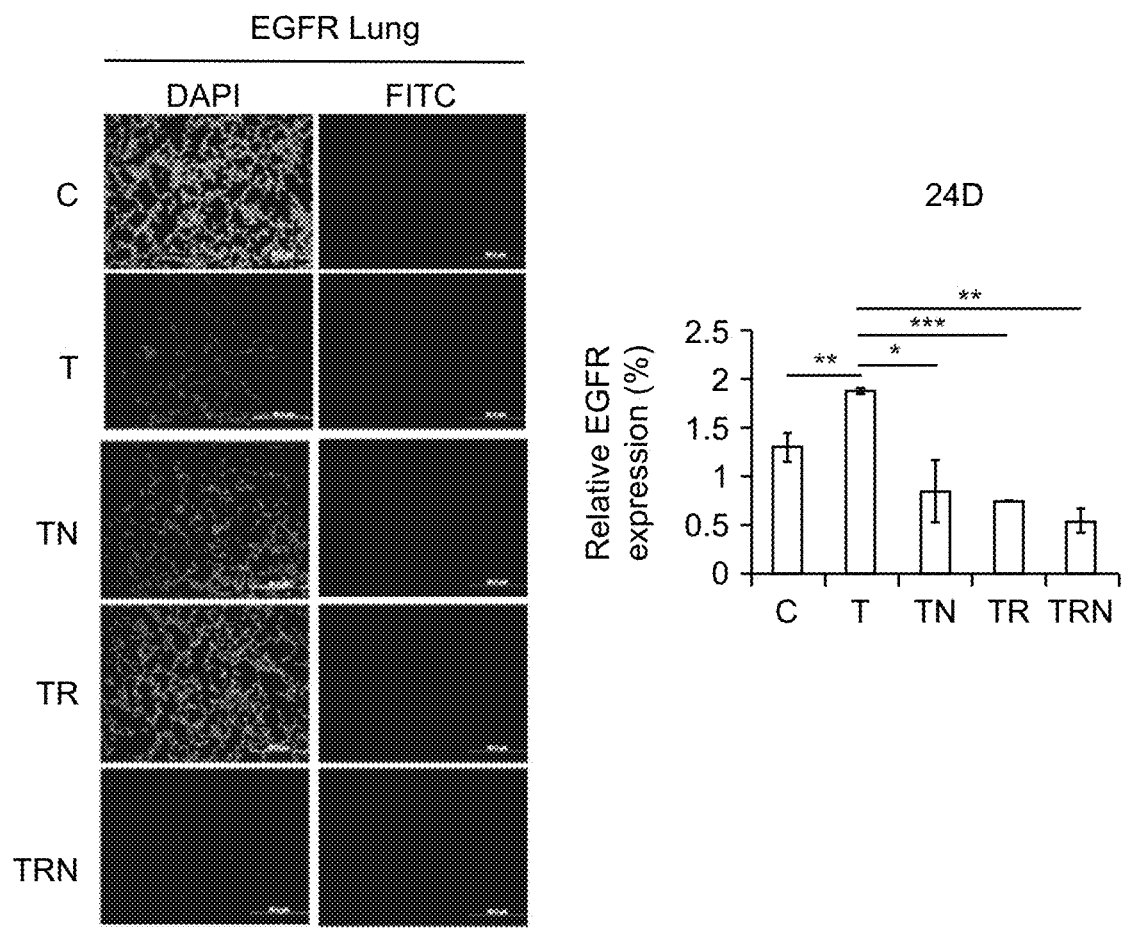
Figure 11D:
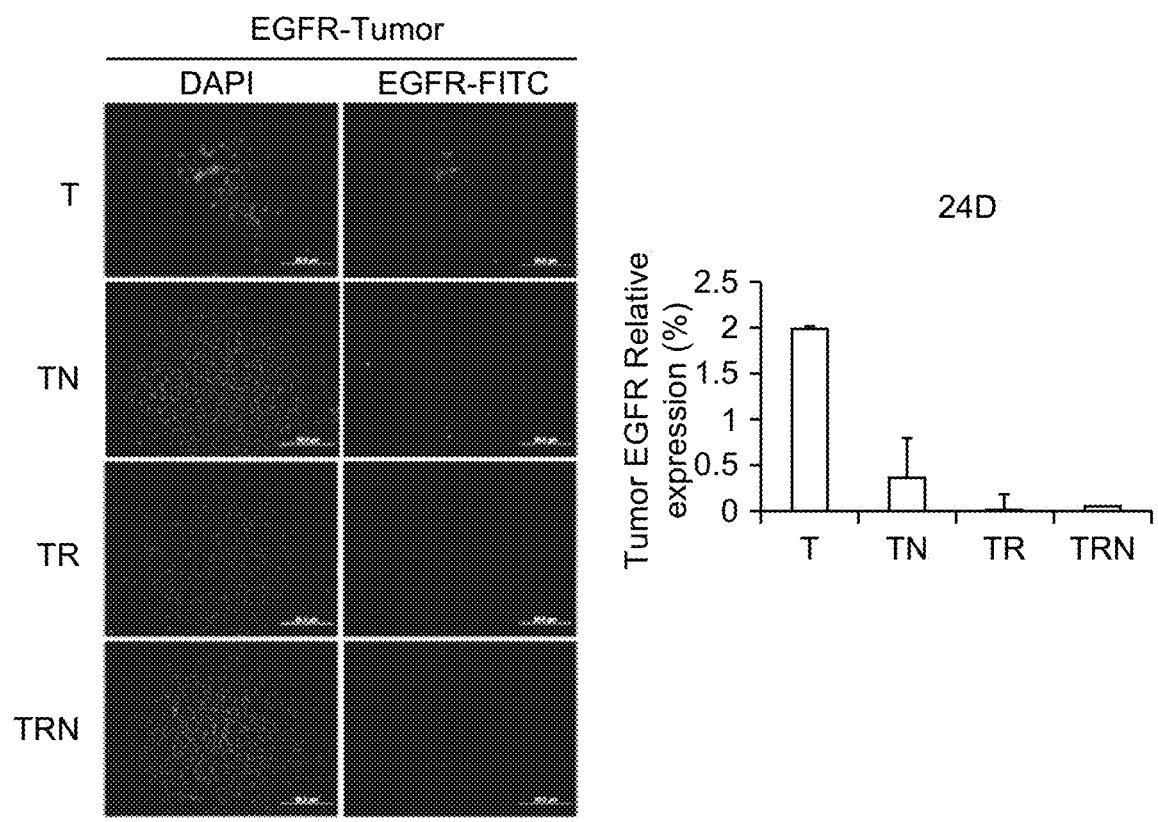

Similar results are found with the expression of EGFR, overexpression of which is associated with tumors. As shown in FIG. 11C, elevated expression of EGFR (left panel, FITC staining) is evident in untreated tumors, and is reduced in subjects treated with a nutritional supplement containing fish oil and selenium, radiotherapy, or cotherapy with such a supplement and radiotherapy. Numerical results are shown in the right panel of FIG. 11C. Similar results are found for EGFR expression of tumors that have metastasized to the lungs, as shown in FIG. 11D. As shown, elevated EGFR expression (left panel, FITC staining) is evident in untreated metastatic sites, and is reduced in subjects treated with a nutritional supplement containing fish oil and selenium or radiotherapy as monotherapies, and with cotherapy using such a supplement and radiotherapy. This suggests that use of a nutritional supplement containing fish oil and selenium, radiotherapy, and/or a combination of treatment with such a supplement and radiotherapy can be effective in enhancing EGFR-directed treatment protocols in individuals receiving treatment for cancer.

Figure 12:
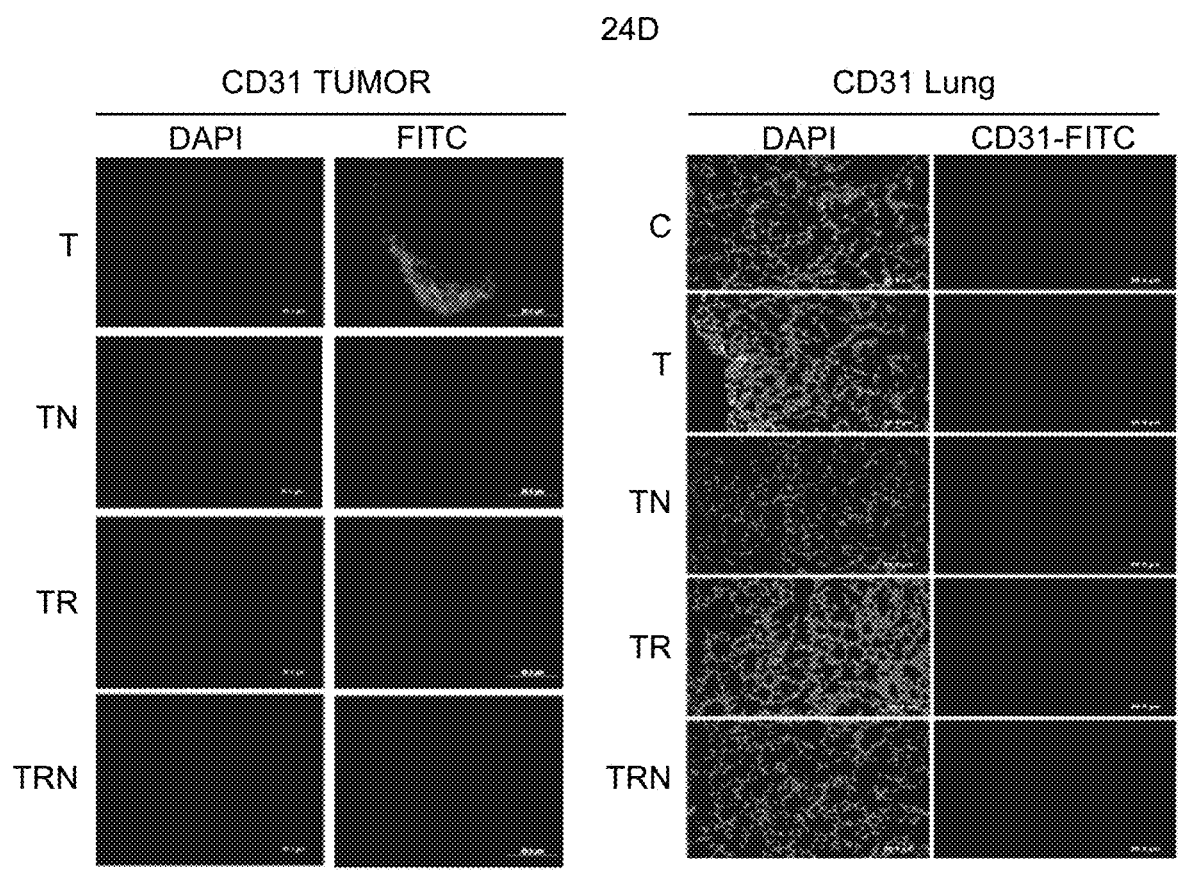
FIG. 12: CD31 (cancer stem cell marker) expression within the tumor mass and in lung tissue (metastasis) 24 days following tumor cell implantation in mice treated as shown in FIG. 9A. FITC represents CD31-specific staining.

Surprisingly, treatment with a nutritional supplement containing fish oil and selenium, radiotherapy, and combined treatment with such a supplement and radiotherapy using the protocol shown in FIG. 9A also has an impact on tumor stem cells. Such stem cells are associated with metastasis and the development of resistance to various cancer therapies. In the following studies the tumor cells selected for implantation are derived from a lung tumor and have a strong tendency to metastasize to the lung from the implantation site. FIG. 12 shows the results of immunocytochemistry studies of different tissues from mice treated with the protocol shown in FIG. 9A. The left panel of FIG. 12 shows the results of staining for CD31 (FITC staining), a stem cell marker, in tumor cells. The right panel shows similar results for metastatic cells in the lungs. Untreated subjects show numerous cells with elevated expression of CD31. Surprisingly, treatment with a nutritional supplement containing fish oil and selenium in the absence of radiotherapy reduces or eliminates the occurrence of cancer stem cells both in the tumor implantation site and at the lung metastatic site.

Figure 13A:
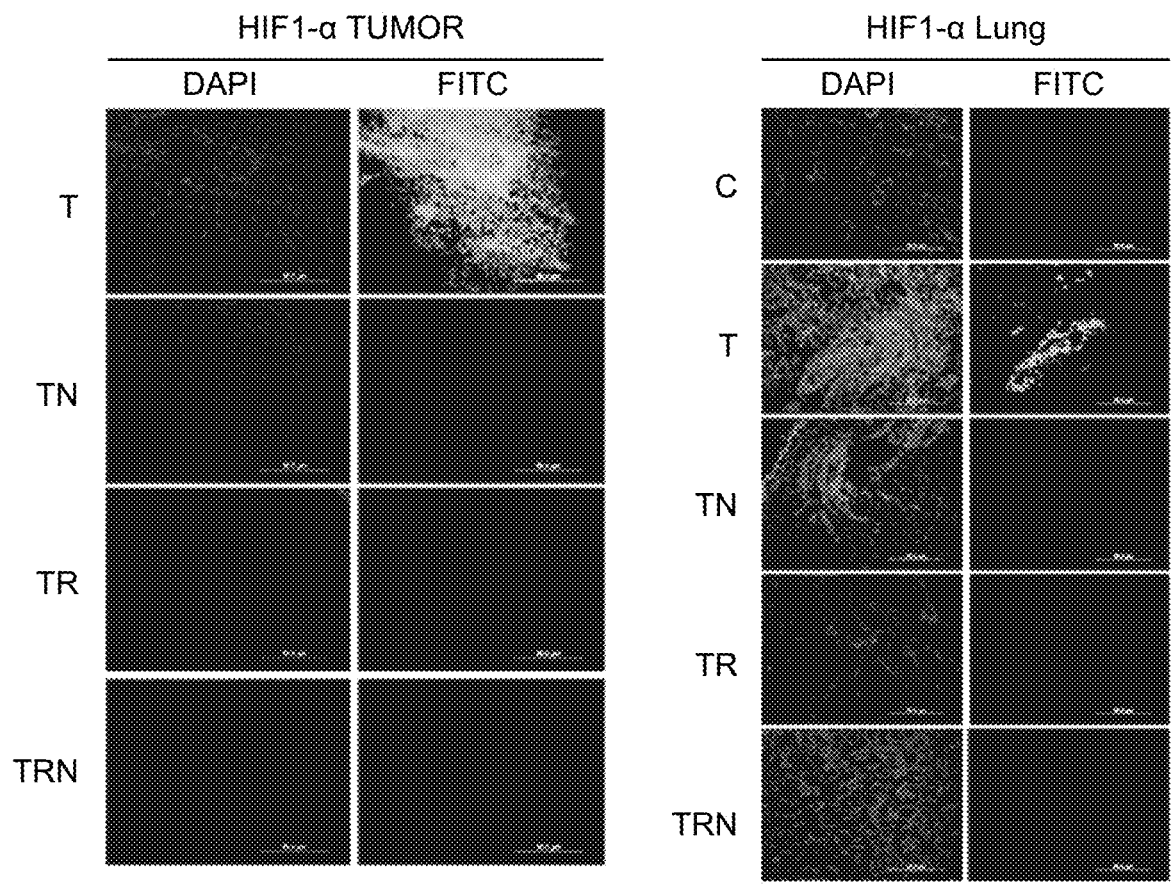
FIGS. 13A and 13B.
Figure 13B:
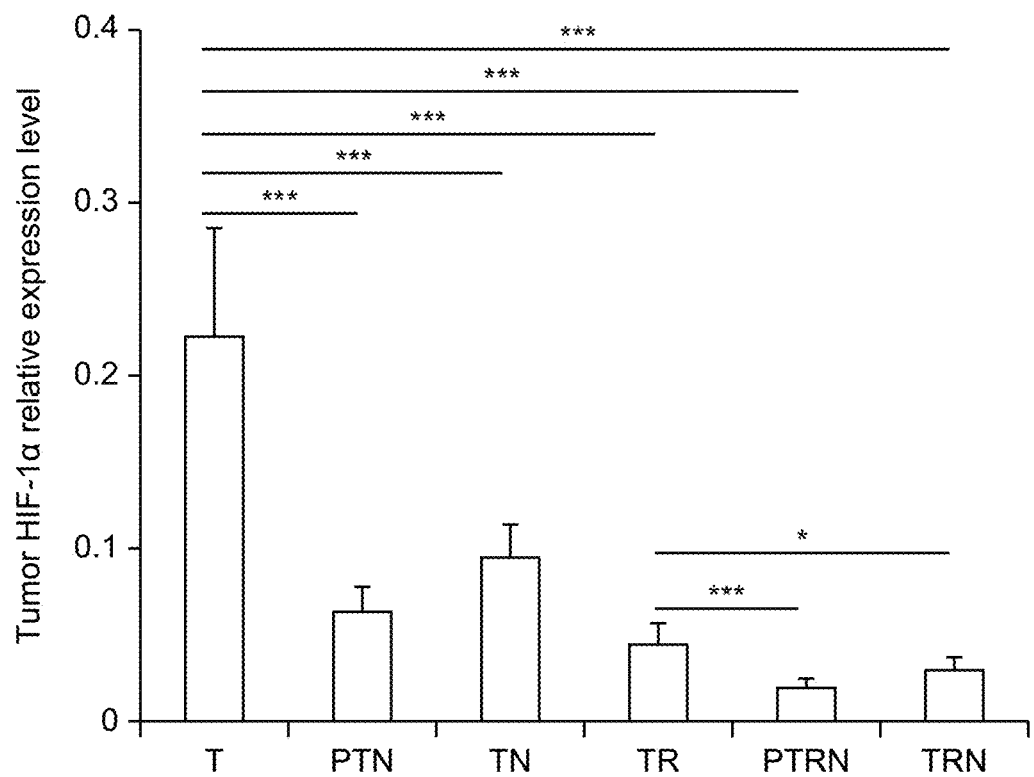

Treatment with a nutritional supplement containing fish oil and selenium, radiotherapy, and combined NutraWell supplementation and radiotherapy using the protocol shown in FIG. 9A also has an impact on hypoxia often found in or among tumor cells. HIF1-α is a marker associated with hypoxia. In the following studies the tumor cells selected for implantation are derived from a lung tumor and have a strong tendency to metastasize to the lung from the implantation site. FIG. 13A shows the results of immunocytochemistry studies of different tissues from mice treated with the protocol shown in FIG. 9A. The left panel shows the results of immunocytochemistry staining for HIF1-α (FITC staining) in tumor cells, while the right panel shows the results of similar staining at lung metastatic sites. Untreated subjects show numerous cells with elevated levels of HIF1-α. Surprisingly, treatment with a nutritional supplement containing fish oil and selenium in the absence of radiotherapy reduces or eliminates the occurrence of such hypoxia markers both in the tumor implantation site and at the lung metastatic site. FIG. 13B shows typical numerical results from a similar study where gene expression in tumor samples was characterized. As shown, both treatment with a supplement containing fish oil and selenium (TN) and pre-treatment with a nutritional supplement containing fish oil and selenium (PTN) for one week reduce tumor expression of HIF1-α, as does radiotherapy (TR). When radiotherapy and such a nutritional supplement are used in combination (PTRN, TRN) a dramatic reduction in tumor HIF1-α expression is evident, particularly in pretreated subjects (PTRN) (which show a synergistic effect). It's evident that use of a nutritional supplement containing fish oil and selenium in combination with radiotherapy can reduce both HIF1-α protein content and gene expression in tumor sites, potentially rendering them more vulnerable to hypoxic conditions.

Treatment with a nutritional supplement containing fish oil and selenium, radiotherapy, and combined supplementation and radiotherapy using the protocol shown in FIG. 9A also has an impact on apoptic activity in tumor cells. Results of qPCR studies for expression of various apoptosis markers (Bax, Bcl-2, and caspase 3) at 24 days from tumor cell implantation in mice is shown in FIG. 14. As shown, the B ax/Bcl-2 expression ratio is low in tumor cells, and only marginally improved by radiotherapy. Surprisingly, treatment with a nutritional supplement containing fish oil and selenium alone provided a significant increase in this ratio. In addition, a pronounced synergistic effect was found on cotherapy with such a supplement and radiotherapy. Caspase 3 expression was actually somewhat suppressed by radiotherapy alone, but was dramatically increased by treatment with a nutritional supplement containing fish oil and selenium, both as a monotherapy and as cotherapy with radiotherapy.

Figure 15A:
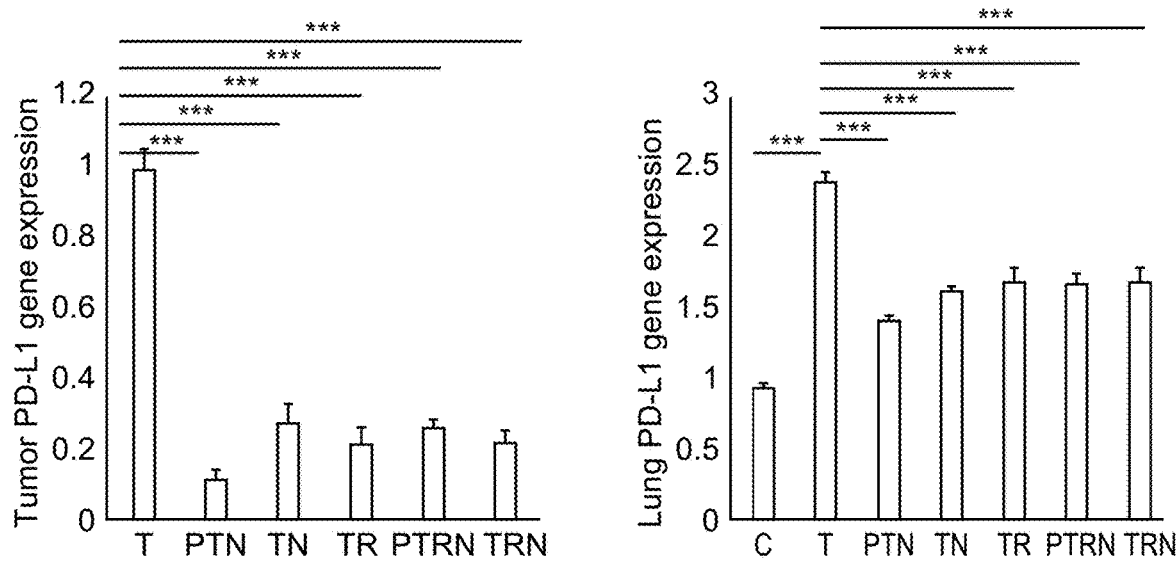
FIGS. 15A and 15B.

Treatment with a nutritional supplement containing fish oil and selenium in combination with radiotherapy has also been found to modulate expression of PDL-1 and PD-1 in primary tumor sites and metastatic (lung) tumor sites in animal models of human disease. As shown in FIG. 15A, both primary (left panel) and metastatic (right panel) tumor cells show high levels of PDL-1 expression (T). Surprisingly, these are markedly reduced by treatment with a nutritional supplement containing fish oil and selenium, both when pretreated (PTN) and treated at the time of implantation (TN). As such, the Inventor believes that such supplements can be used to enhance immunotherapeutic approaches to cancer treatment. Treatment with radiotherapy (TR) also shows a reduction in PD-L1 gene expression in both primary and metastatic sites, suggesting that radiotherapy alone can be used to enhance immunotherapeutic approaches to cancer treatment. Cotherapy with such a nutritional supplement and radiotherapy is effective in reducing PDL-1 expression in both primary tumor sites and metastatic sites, whether the supplement is provided prior to implantation (PTRN) or at the time of implantation (TRN). Surprisingly, the effects are more marked at the primary tumor site than at metastatic sites. This suggests that cotherapy with a nutritional supplement that includes fish oil and selenium in combination with radiotherapy can render tumor cells at both primary and metastatic sites more susceptible to the patient's immune system, and/or can enhance the effect of immunotherapy approaches to cancer treatment.

Figure 15B:
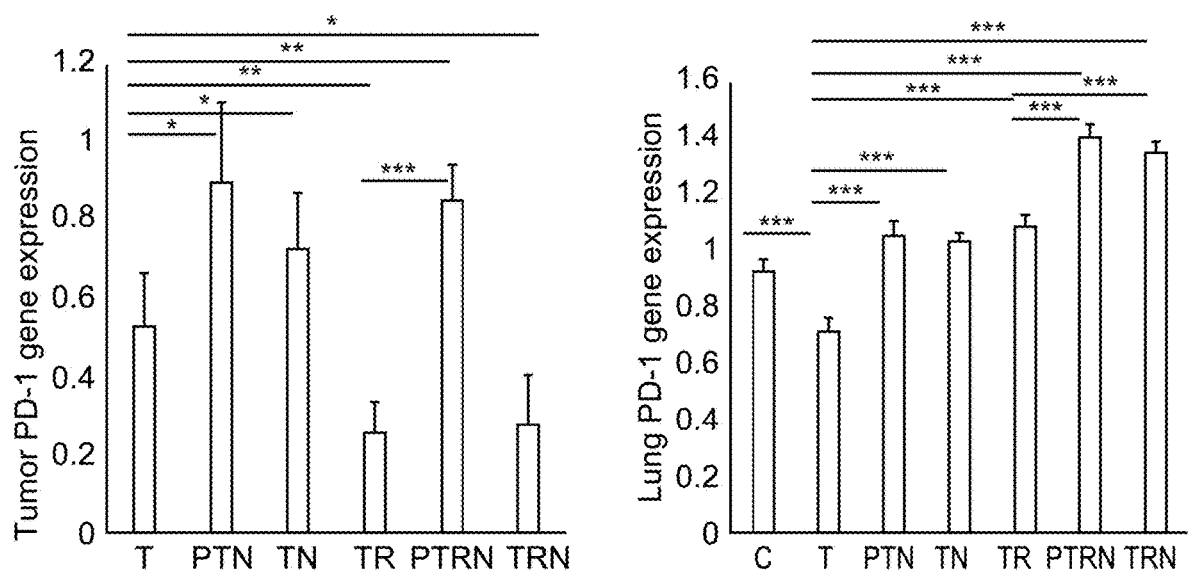

Similar studies were performed on PD-1 expression. As shown in FIG. 15B, PD-1 expression is reduced in primary site tumor cells treated with radiotherapy (TR) and enhanced in primary site tumor cells (left panel) in animals treated with a supplement containing fish oil and selenium, either prior to implantation (PTN) or upon implantation (TN). Cotherapy with the nutritional supplement and radiotherapy provides differential results depending on if the supplement is provided prior to implantation (PTRN) or at the time of implantation (TRN). As shown in the right panel of FIG. 15B, tumor cells at metastatic sites showed reduced PD-1 expression relative to samples taken from control animals. Surprisingly, radiotherapy resulted in an increase in PD-1 expression at metastatic sites (right panel), as did treatment with a supplement containing fish oil and selenium either prior to implantation or at the time of implantation. Cotherapy with radiotherapy and such a supplement provided higher levels of PD-1 expression than those observed with monotherapy. It is apparent that treatment with a nutritional supplement containing fish oil and selenium, particularly in combination with radiotherapy, can shift PD-1 expression away from reduced expression levels seen in tumor-bearing subjects, particularly in metastatic sites.

Figures 16A, 16B:
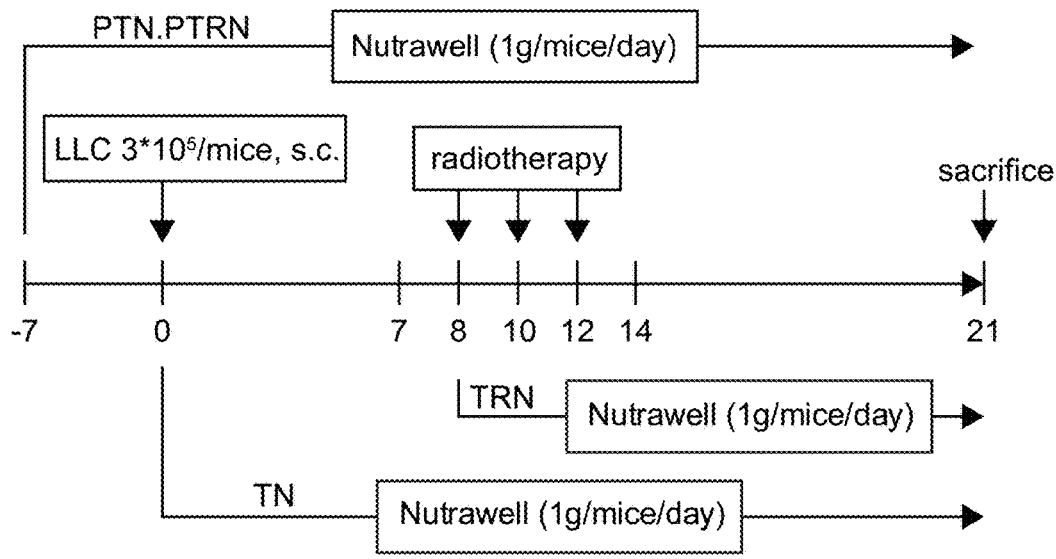
FIGS. 16A and 16B.

Preimplantation, Preradiotherapy, and Initiation of Radiotherapy Supplementation with Repeated Radiotherapy Another treatment protocol combining both pretreatment with a nutritional supplement containing fish oil and selenium and multiple rounds of radiotherapy typical of clinical application is shown in FIGS. 16A and 16B. In this protocol treatment with the supplement was initiated prior to tumor cell implantation, at the time of tumor cell implantation, and at the initiation of radiotherapy.

Figure 17:
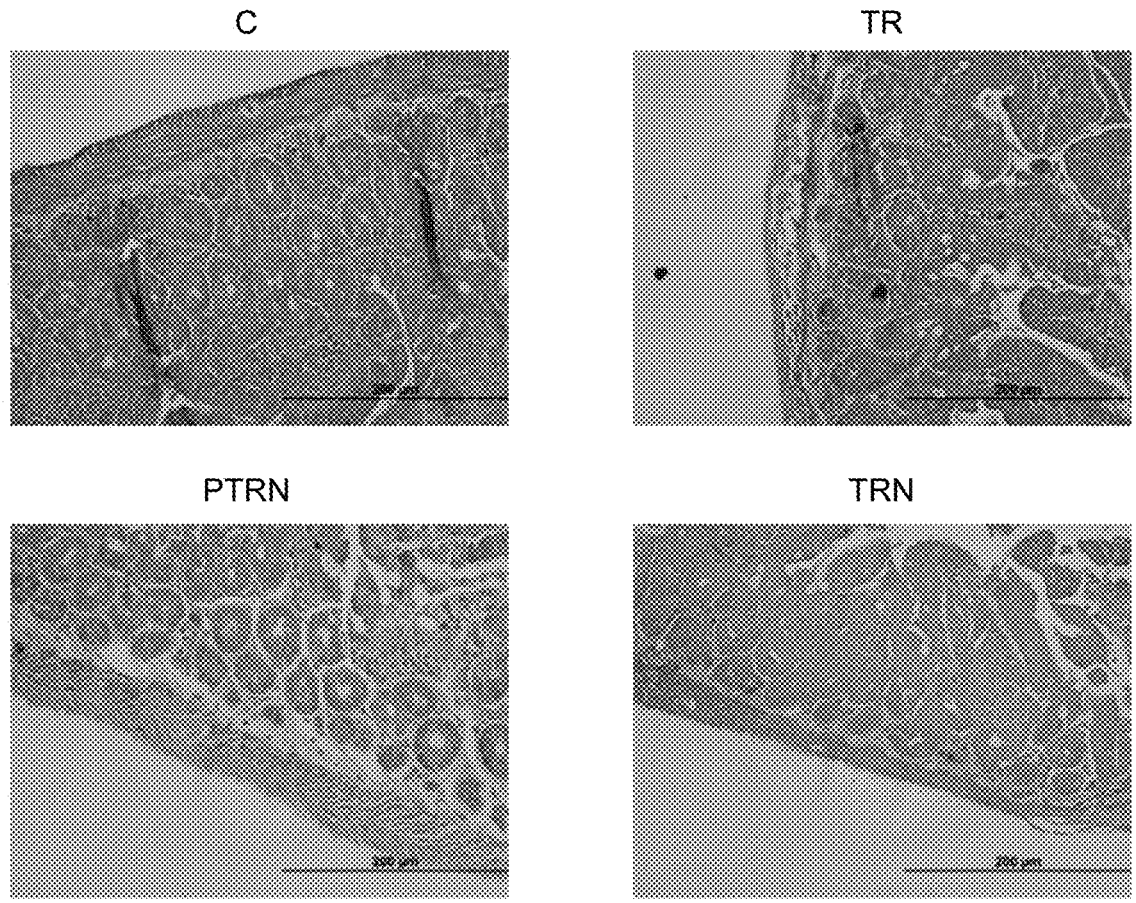
FIG. 17: Photomicrographs of cross sections of the intestines of mice treated by the protocol described in FIG. 16A.

Loss of intestinal absorption and the resulting malnutrition are a well known side effect of radiotherapy, particularly repeated radiotherapy. FIG. 17 shows photomicrographs that demonstrate the effect treatment with a nutritional supplement containing fish oil and selenium on the cellular architecture of the gut during radiotherapy. Cellular architecture of the gut is shown for untreated control subjects (top left panel), tumor implanted subjects treated with multiple rounds of radiotherapy (to right panel), tumor implanted subjects pretreated with a nutritional supplement containing fish oil and selenium and subsequently treated with radiotherapy (lower left panel), and tumor implanted subjects treated with a nutritional supplement containing fish oil and selenium at the time of initiation of radiotherapy (lower right panel). As shown, treatment with a nutritional supplement containing fish oil and selenium can maintain the intestinal brush border during radiotherapy, with pretreatment apparently enhancing the intestinal brush border. This indicates that treatment with such a supplement, particularly pretreatment, can effectively address side effects of radiotherapy.

Figure 18A:
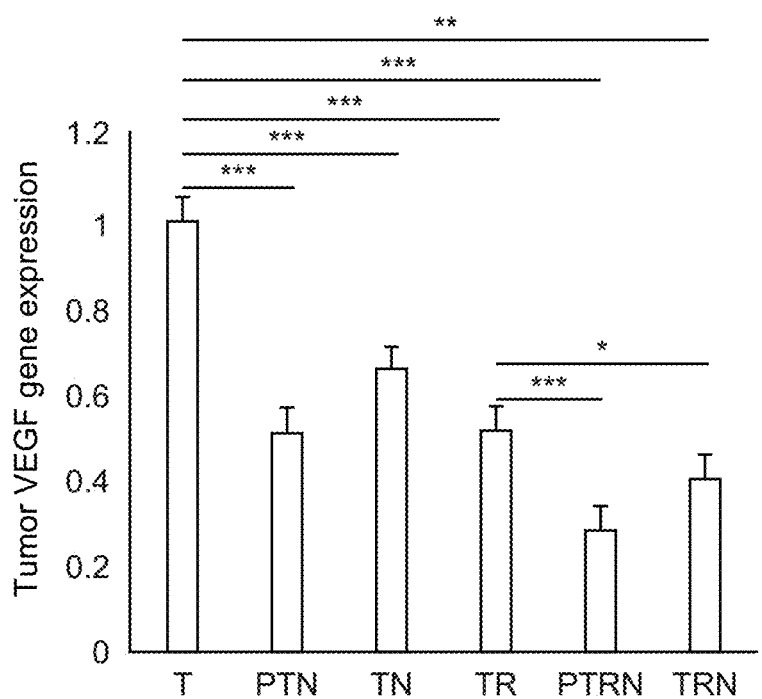
FIGS. 18A to 18F.

Such a treatment protocol has been found to modify expression of certain genes in tumor cells in vivo. Results of qPCR studies of gene expression (e.g. angiogenic factor-related, apoptosis-related, etc.) in tumor cells from mice treated by the protocol shown in FIG. 16A are shown in FIGS. 18A to 18F. As shown in FIG. 18A, treatment with a nutritional supplement containing fish oil and selenium reduces VEGF expression in tumor cells, as does repeated radiotherapy. Combined therapy with such a supplement and radiotherapy provides an enhanced reduction in VEGF expression, particularly when a nutritional supplement containing fish oil and selenium is provided prior to initiation of radiotherapy.

Figure 18B:
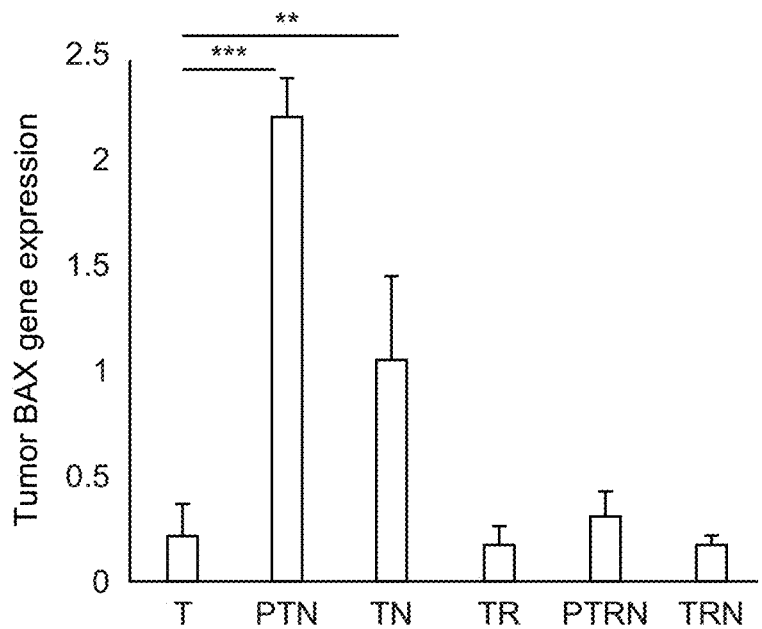

FIG. 18B shows that BAX expression in tumor cells is increased by treatment with a nutritional supplement containing fish oil and selenium, and relatively unaffected by repeated radiotherapy alone. Pretreatment with such a supplement in combination with repeated radiotherapy also increased BAX expression. Similar results are found for expression of another apoptosis-related gene (Caspase 3), as shown in FIG. 18D. Results of studies of Caspase-3 expression in metastatic (lung) tumors are shown in FIG. 18F. As shown, expression of Caspase-3 in such metastatic tumors is elevated by treatment with a nutritional supplement containing fish oil and selenium and by repeated radiotherapy, and is similar to that of control cells when the supplement is provided as cotherapy prior to initiation of radiotherapy.

Figure 18C:
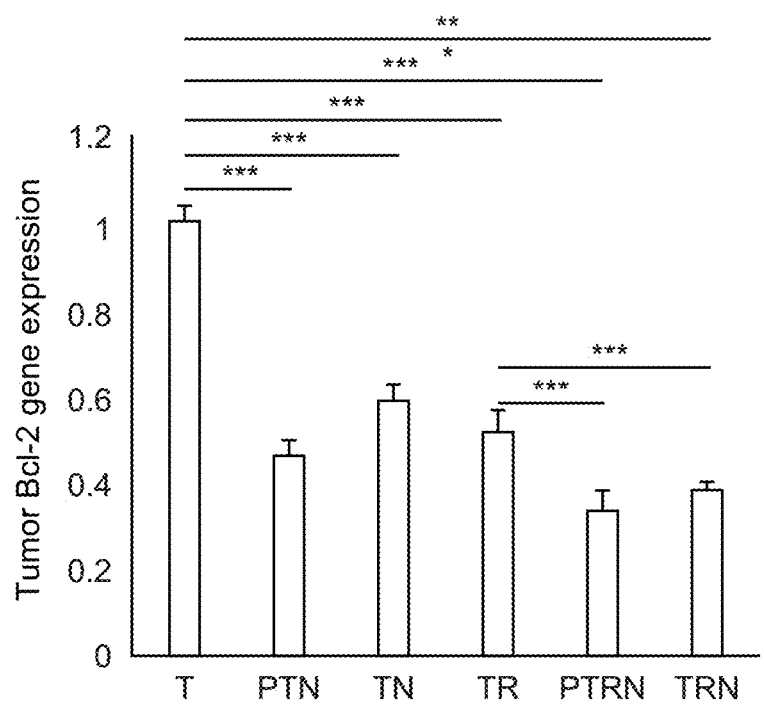
Figure 18D:
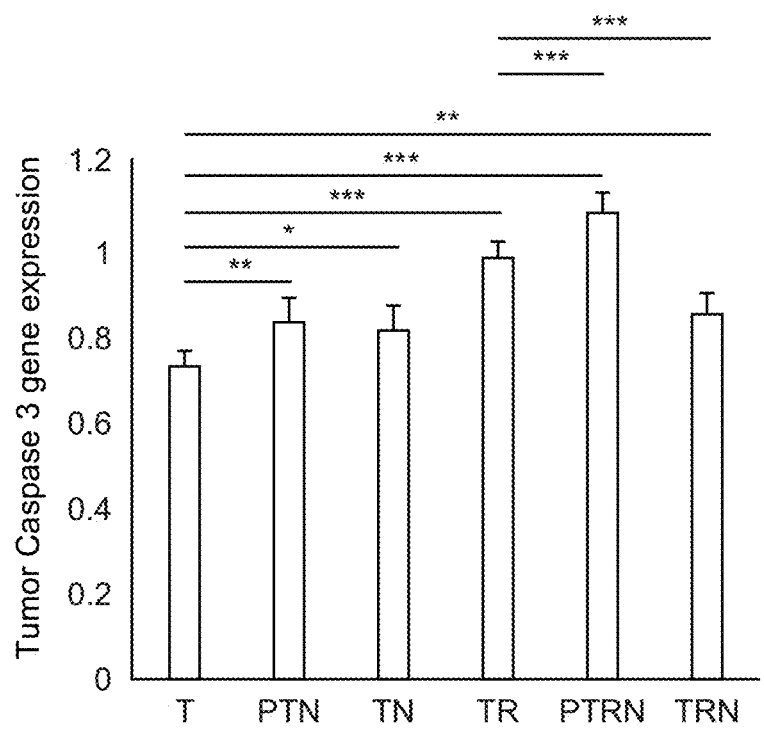
Figure 18E:
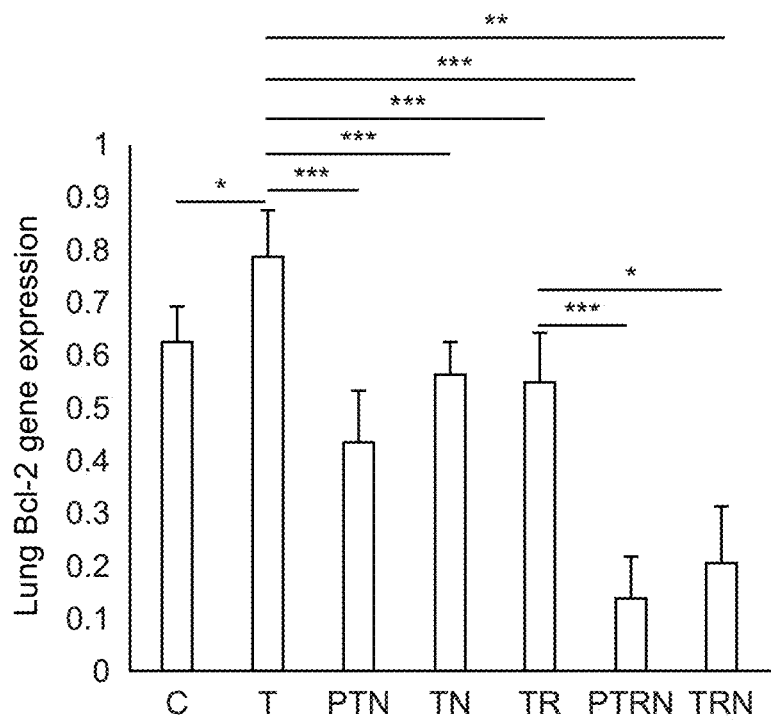
Figure 18F:
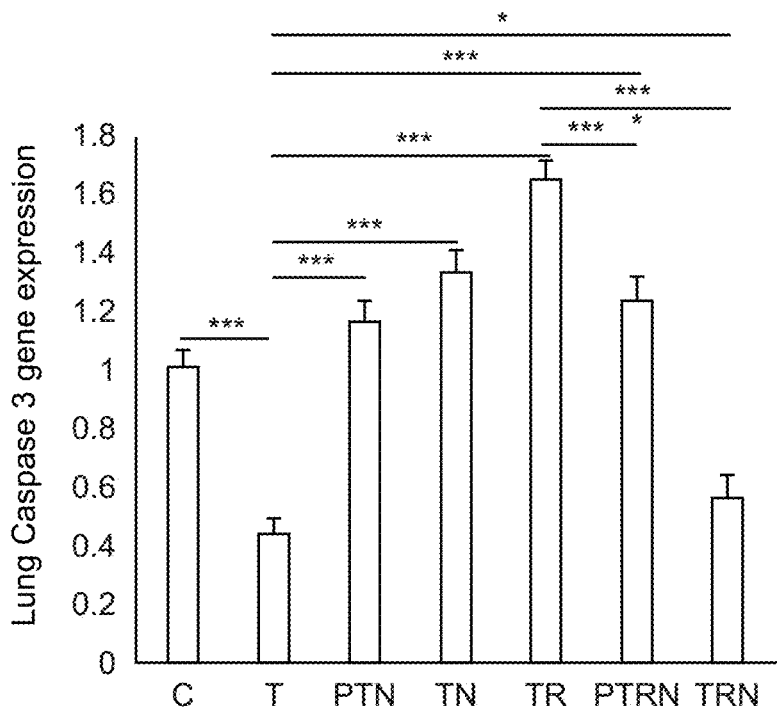

Expression of another apoptosis-related gene, Bcl-2, in tumor cells is reduced by treatment with a nutritional supplement containing fish oil and selenium and by repeated radiotherapy alone (see FIG. 18C). This reduction in Bcl-2 expression is more pronounced on cotherapy with such a supplement and repeated radiotherapy, particularly when the supplement is provided prior to initiation of radiotherapy. FIG. 18E shows the results of similar studies performed on metastatic (lung) tumors. As shown, the reduction in Bcl-2 expression is reduced in a synergistic fashion on cotherapy with a nutritional supplement containing fish oil and selenium and repeated radiotherapy, particularly when the supplement is provided prior to initiation of radiotherapy.

Pre-Implantation Supplementation and Repeated Radiotherapy

Figures 19A, 19B:
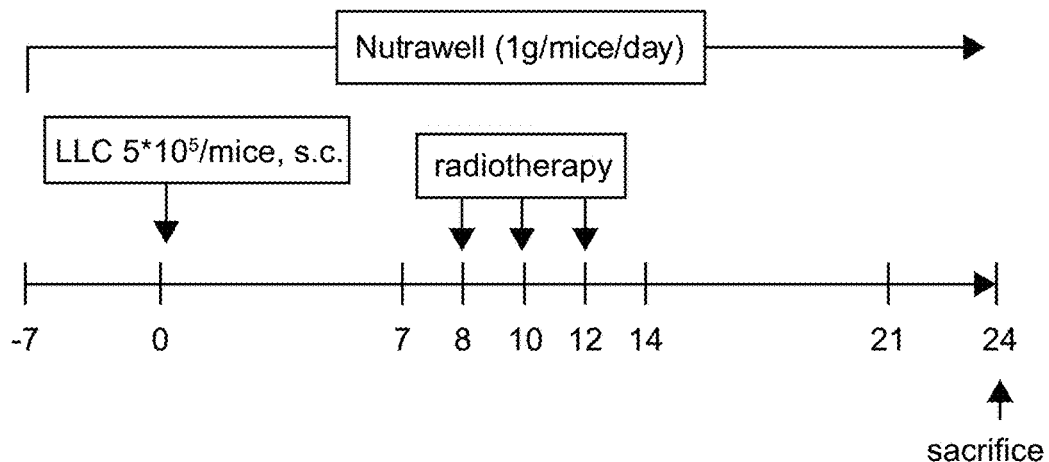
FIGS. 19A and 19B.

FIGS. 19A and 19B show a treatment protocol and related test groups (respectively) where a nutritional supplement containing fish oil and selenium is provided 7 days prior to implantation of tumor cells, with radiotherapy taking place on days 8, 10, and 12 following implantation. Mice were sacrificed on day 24 following implantation.

Figure 20A:
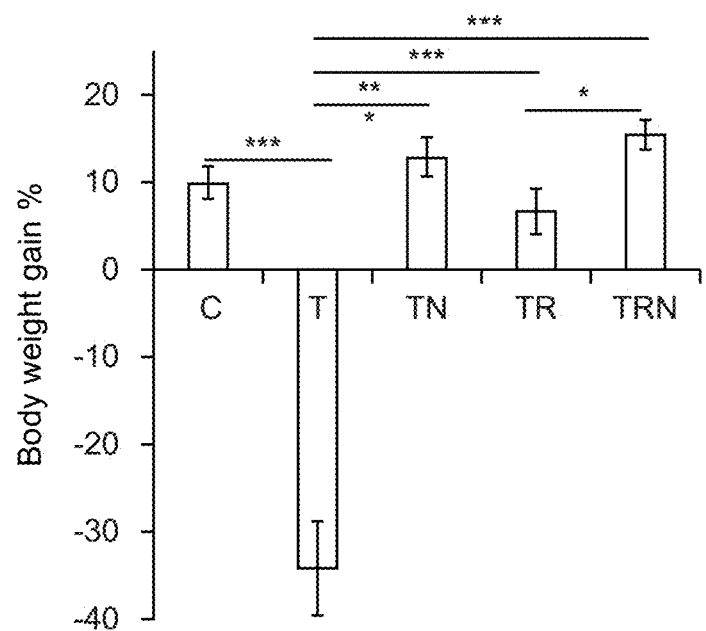
FIGS. 20A and 20B.
Figure 20B:
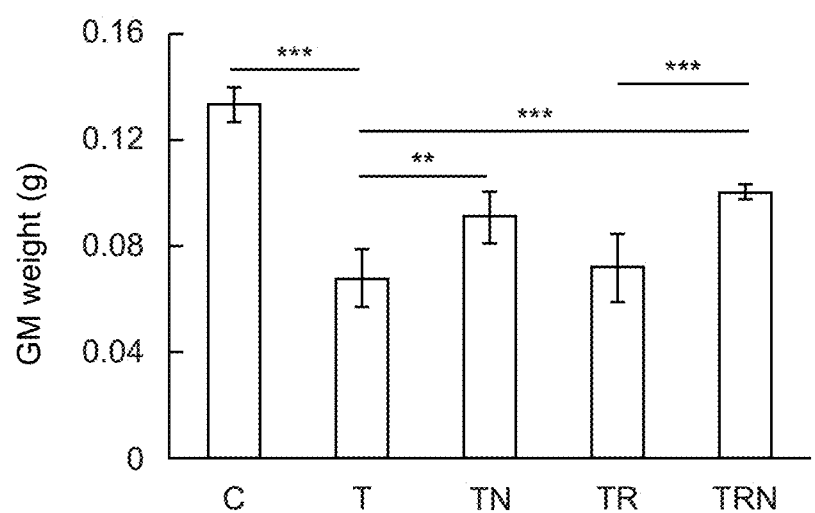

A well known side effect of both cancer and repeated radiotherapy is weight loss. This can be due to wasting associated with disease and with side effects of radiotherapy. The effect of treatment with a nutritional supplement containing fish oil and selenium on loss of body mass and on muscle mass following repeated radiotherapy is shown in FIGS. 20A and 20B. It should be appreciated that body mass was characterized following removal of the tumor mass. As shown in FIG. 20A, when tumor mass is removed a significant decrease in remaining body mass is apparent relative to control subjects. This is improved by treatment with a nutritional supplement containing fish oil and selenium and by radiotherapy as monotherapies. Surprisingly, gains in body mass surpass those of control subjects when such a supplement and repeated radiotherapy are used in combination. FIG. 20B shows the weight of gastrocnemius muscle in the various test groups. Loss of muscle mass is apparent in untreated tumor bearing animals. This is marginally improved by repeated radiotherapy alone. Surprisingly, treatment with a nutritional supplement containing fish oil and selenium provides significant retention in muscle mass. Cotherapy with a nutritional supplement containing fish oil and selenium and repeated radiotherapy provides a synergistic improvement in muscle mass relative to untreated tumor bearing subjects. It is apparent that pre-treatment with a nutritional supplement containing fish oil and selenium effectively reverses the loss of body mass (relative to control subjects) and muscle mass resulting from both the presence of the tumor and repeated radiotherapy.

Preimplantation Supplementation and Repeated Radiotherapy

Figures 21A, 21B:
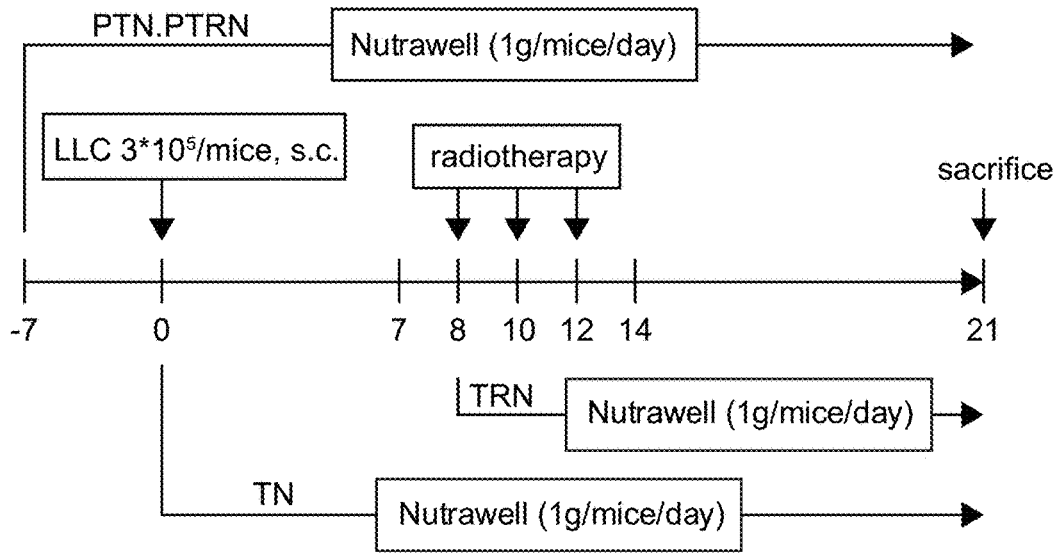
FIGS. 21A and 21B.

Another treatment protocol with related treatment groups is shown in FIGS. 21A and 21B, which is similar to the protocol shown in FIGS. 16A and 16B. In this protocol radiotherapy is provided on days 8, 10, and 12 following implantation of tumor cells. Treatment with a nutritional supplement containing fish oil and selenium is provided either 7 days prior to implantation, the day of implantation, or on the initiation of radiotherapy. Mice were sacrificed on day 21 following tumor cell implantation.

Figure 22:
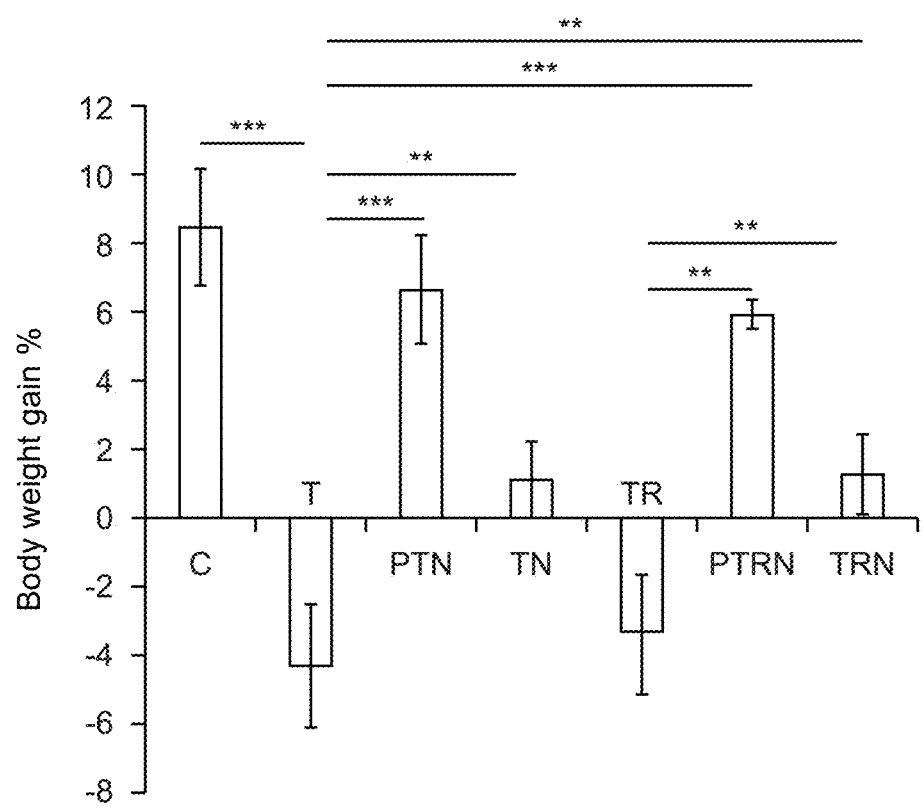
FIG. 22: Effect of NutraWell supplementation on body mass in mice receiving repeated radiotherapy following tumor cell implantation using the protocol shown in FIG. 21A.

A well known side effect of both cancer and radiotherapy is weight loss. The effect of treatment with a nutritional supplement containing fish oil and selenium on loss of body mass and loss of muscle mass when provided prior to and when provided coincident with the initiation of repeated radiotherapy is shown in FIG. 22. It should be appreciated that body mass was characterized following removal of the tumor mass. As shown, body weight gains over time of untreated tumor bearing subjects (following excision of the tumor) are dramatically reduced relative to control subjects. Similar losses are noted on repeated radiotherapy when used alone. Surprisingly, treatment with a nutritional supplement containing fish oil and selenium provides remarkably improved body weight gains over time, both as a monotherapy and when used in combination with repeated radiotherapy. This is particularly evident with such a supplement is used as a pretreatment.

Figure 23:
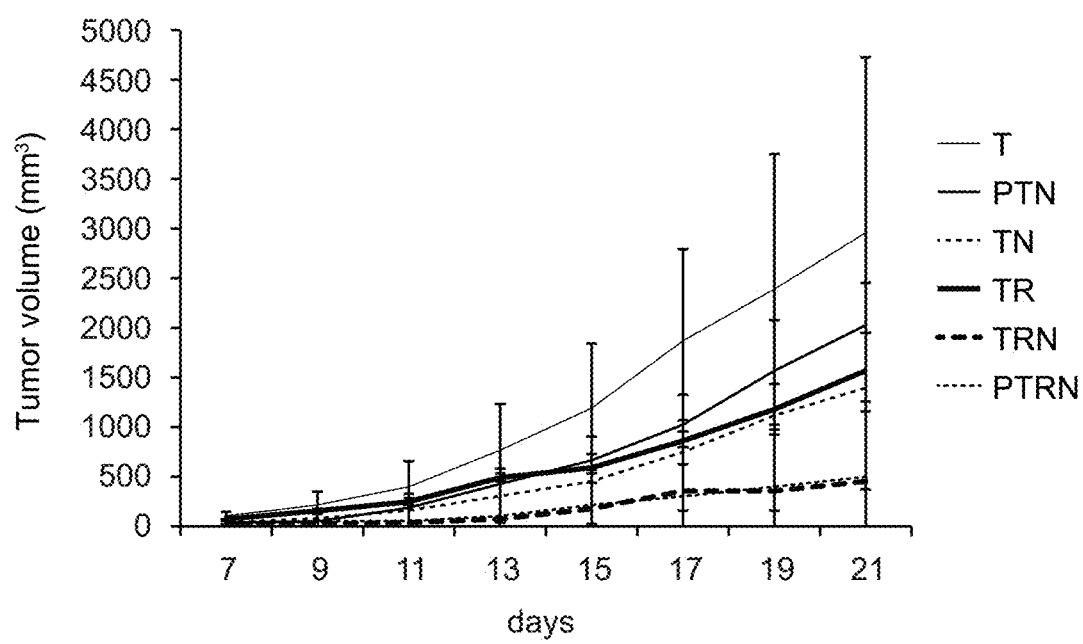
FIG. 23: Changes in tumor volume over time on repeated radiotherapy in combination with NutraWell supplement in mice treated as in the protocol shown in FIG. 21A.

Inventors have also found that pre-treatment with a nutritional supplement containing fish oil and selenium enhances the reduction in tumor volume seen on repeated radiotherapy, as shown in FIG. 23. As shown, both repeated radiotherapy and treatment with a nutritional supplement containing fish oil and selenium have a moderate effect in reducing tumor volume relative to tumors of untreated tumor bearing animals. Surprisingly, tumor volume shows almost no change over time when repeated radiotherapy and a nutritional supplement containing fish oil and selenium are used as cotherapies, indicating a synergistic effect.

Figure 24A:
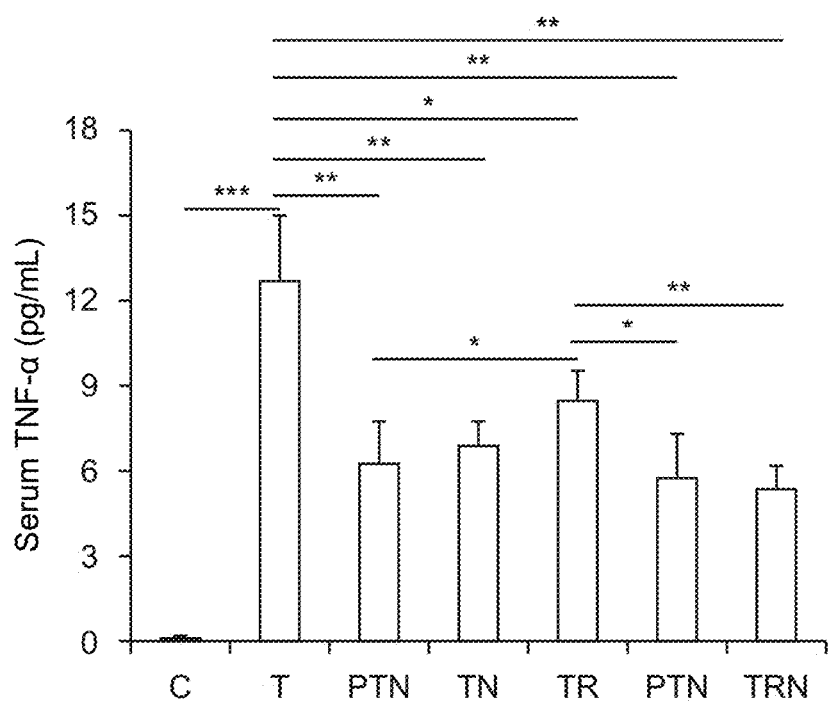
FIGS. 24A and 24B.
Figure 24B:
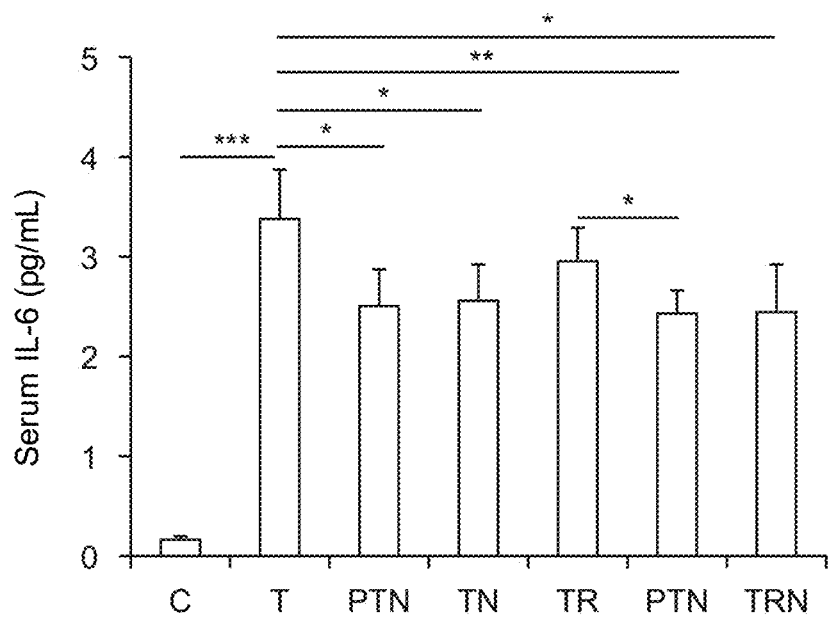

The presence of tumors and repeated radiotherapy can also result in the development of inflammation, which can be characterized by the presence of pro-inflammatory cytokines in serum. FIGS. 24A and 24B show the effect of administration of a nutritional supplement containing fish oil and selenium with repeated radiotherapy on the concentration of pro-inflammatory cytokines in mice treated as in the protocol shown in FIG. 21A. FIG. 24A shows values for serum TNF-α. It is apparent that untreated tumor bearing animals show highly elevated concentrations of TNF-α, which is reduced to some extent by repeated radiotherapy. Treatment with a nutritional supplement containing fish oil and selenium also resulted in a reduction in serum TNF-α, particularly when such a supplement was used in cotherapy with repeated radiotherapy. FIG. 24B shows the results of similar studies where the serum concentration of IL-6 was characterized, which show similar results.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of decreasing angiogenesis, comprising:
providing than individual with a nutritional supplement comprising 10,000 to 50,000 mg maltodextrin; 5,000 to 60,000 mg whey protein isolate; 1,000 to 50,000 mg whey protein concentrate; 40 to 15,000 mg fructooligosaccharides/inulin; 1,000 to 9,000 mg granulated honey; 500 to 15,000 mg oat fiber; 500 to 20,000 mg natural French Vanilla flavor; 500 to 50,000 mg soy protein; 500 to 10,000 mg brownulated powdered brown sugar; 500 to 5,000 mg natural vanilla masking flavor; 200 to 10,000 mg lecithin; 50 to 5,000 mg non-fat milk; 50 to 5,000 mg rice protein powder; 50 to 2,000 mg calcium caseinate; 100 to 7,000 mg flax seed oil; 100 to 7,000 mg canola oil; 100 to 7,000 mg borage oil; 10 to 7,000 mg olive oil; 150 to 10,000 mg, fish oil; 100 to 1,000 mg pure lemon oil; 50 to 1,000 mg pure orange oil; 0.5 to 200 mg mixed tocopherols; 200 to 1,500 mg potassium phosphate; 100 to 5,000 mg calcium carbonate; 150 to 2,500 mg choline bitartrate; 100 to 2,000 mg sodium chloride; 100 to 2,000 mg calcium phosphate tribasic; 50 to 3,000 mg ascorbic acid; 50 to 2,000 mg potassium chloride; 50 to 500 mg magnesium oxide; 30 to 4,000 mcg selenium yeast; 30 to 3,000 mcg chromium yeast; 30 to 2,000 mcg molybdenum yeast; 10 to 5,000 mg inositol; 5 to 200 mg zinc sulfate monohydrate; 5 to 2,000 IU dry vitamin E acetate; 5 to 500 mg niacinamide; 3 to 100 mg ferric orthophosphate; 3 to 200 mg calcium pantothenate; 3 to 100 mg manganese sulfate monohydrate; 1 to 100 mg beta carotene; 1 to 15 mg copper gluconate; 25 to 5,000 IU vitamin D3; 2 to 1000 mcg vitamin K2; 0.5 to 200 mg pyridoxine HCl; 0.5 to 1,500 mg potassium iodide; 0.5 to 1,000 mg riboflavin; 0.5 to 2,500 mg thiamine hydrochloride; 1 to 500 mcg dry vitamin K1; 500 to 100,000 IU vitamin A acetate; 100 to 10,000 mcg folic acid; 10 to 10,000 mcg d-biotin; 1 to 3,000 mcg vitamin B12; 300 to 30,000 mg L-carnitine; 500 to 60,000 mg L-glutamine; 500 to 30,000 mg L-arginine base; 50 to 2,000 mg taurine; 50 to 2,000 mg L-lysine; 10 to 1,000 mg alpha lipoic acid; 15 to 1,500 mg resveratrol; 10 to 5,000 mg co-enzyme Q10; 5 to 1,000 mg glycine; 5 to 1,000 mg proline; 2 to 500 mg Lact. acidophilus; 2 to 500 mg Bifido bifidium; 2 to 500 mg Lac. bulgaricus; 2 to 500 mg Bifido longum; 2 to 500 mg Strep. thermophilus; 5 to 100 mg papain; 5 to 100 mg pepsin; 5 to 100 mg lipase; 5 to 100 mg bromelain; 0.5 to 100 mg pancreatin 4X; 1 to 100 mg lactase; 3 to 100 mg betaine HCl; 2 to 500 mg pineapple juice powder; 2 to 500 mg papaya fruit powder; 30 to 3,000 mg quercetin; 25 to 600 mg epigallocatechin gallate (EGCG); 15 to 500 mg oligomeric proanthocyanidin (OPC); 15 to 5,000 mg anthocyanins; 10 to 300 mg ellagic acid; 2 to 90 mg astaxanthin; 20 to 1,500 mg fucoidan; 5 to 6,000 mg Cordyceps; 15 to 10,000 mg Ganoderma Lucidum; 40 to 15,000 mg Shiitake; 30 to 15,000 mg Maitake; and 30 to 15000 mg Turkey Tail; and applying a radiotherapy protocol to the individual, wherein the nutritional supplement is provided in an amount effective to reduce angiogenesis in the individual.

2. The method of claim 1, wherein the nutritional supplement is provided concurrent with the radiotherapy protocol.

3. A method of reducing cancer stem cell content of a tumor, comprising:

providing a patient having a tumor with a nutritional supplement comprising an effective amount of fish oil and an effective amount of selenium; and applying a radiotherapy protocol, wherein the nutritional supplement is provided in an amount effective to reduce occurrence of cancer stem cells in the tumor, wherein the nutritional supplement comprises 10,000 to 50,000 mg maltodextrin; 5,000 to 60,000 mg whey protein isolate; 1,000 to 50,000 mg whey protein concentrate; 40 to 15,000 mg fructooligosaccharides/inulin; 1,000 to 9,000 mg granulated honey; 500 to 15,000 mg oat fiber; 500 to 20,000 mg natural French Vanilla flavor; 500 to 50,000 mg soy protein; 500 to 10,000 mg brownulated powdered brown sugar; 500 to 5,000 mg natural vanilla masking flavor; 200 to 10,000 mg lecithin; 50 to 5,000 mg non-fat milk; 50 to 5,000 mg rice protein powder; 50 to 2,000 mg calcium caseinate; 100 to 7,000 mg flax seed oil; 100 to 7,000 mg canola oil; 100 to 7,000 mg borage oil; 10 to 7,000 mg olive oil; 150 to 10,000 mg fish Oil; 100 to 1,000 mg pure lemon oil; 50 to 1,000 mg pure orange oil; 0.5 to 200 mg mixed tocopherols; 200 to 1,500 mg potassium phosphate; 100 to 5,000 mg calcium carbonate; 150 to 2,500 mg choline bitartrate; 100 to 2,000 mg sodium chloride; 100 to 2,000 mg calcium phosphate tribasic; 50 to 3,000 mg ascorbic acid; 50 to 2,000 mg potassium chloride; 50 to 500 mg magnesium oxide; 30 to 4,000 mcg selenium yeast; 30 to 3,000 mcg chromium yeast; 30 to 2,000 mcg molybdenum yeast; 10 to 5,000 mg inositol; 5 to 200 mg zinc sulfate monohydrate; 5 to 2,000 IU dry vitamin E acetate; 5 to 500 mg niacinamide; 3 to 100 mg ferric orthophosphate; 3 to 200 mg calcium pantothenate; 3 to 100 mg manganese sulfate monohydrate; 1 to 100 mg beta carotene; 1 to 15 mg copper gluconate; 25 to 5,000 IU vitamin D3; 2 to 1000 mcg vitamin K2; 0.5 to 200 mg pyridoxine HCl; 0.5 to 1,500 mg potassium iodide; 0.5 to 1,000 mg riboflavin; 0.5 to 2,500 mg thiamine hydrochloride; 1 to 500 mcg dry vitamin K1; 500 to 100,000 IU vitamin A acetate; 100 to 10,000 mcg folic acid; 10 to 10,000 mcg d-biotin; 1 to 3,000 mcg vitamin B12; 300 to 30,000 mg L-carnitine; 500 to 60,000 mg L-glutamine; 500 to 30,000 mg L-arginine base; 50 to 2,000 mg taurine; 50 to 2,000 mg L-lysine; 10 to 1,000 mg alpha lipoic acid; 15 to 1,500 mg resveratrol; 10 to 5,000 mg co-enzyme Q10; 5 to 1,000 mg glycine; 5 to 1,000 mg proline; 2 to 500 mg Lact. acidophilus; 2 to 500 mg Bifido bifidium; 2 to 500 mg Lac. bulgaricus; 2 to 500 mg Bifido longum; 2 to 500 mg Strep. thermophilus; 5 to 100 mg papain; 5 to 100 mg pepsin; 5 to 100 mg lipase; 5 to 100 mg bromelain; 0.5 to 100 mg pancreatin 4X; 1 to 100 mg lactase; 3 to 100 mg betaine HCl; 2 to 500 mg pineapple juice powder; 2 to 500 mg papaya fruit powder; 30 to 3,000 mg quercetin; 25 to 600 mg epigallocatechin gallate (EGCG); 15 to 500 mg oligomeric proanthocyanidin (OPC); 15 to 5,000 mg anthocyanins; 10 to 300 mg ellagic acid; 2 to 90 mg astaxanthin; 20 to 1,500 mg fucoidan; 5 to 6,000 mg Cordyceps; 15 to 10,000 mg Ganoderma Lucidum; 40 to 15,000 mg Shiitake; 30 to 15,000 mg Maitake; and 30 to 15000 mg Turkey Tail.

4. The method of claim 3, wherein the nutritional supplement is provided concurrent with the radiotherapy protocol.

* * * * *